United States Patent
Trout et al.

(10) Patent No.: US 9,777,067 B2
(45) Date of Patent: Oct. 3, 2017

(54) HER2- AND VEGF-A-BINDING PROTEINS WITH ENHANCED STABILITY

(71) Applicant: Massachusetts Institute of Technology, Cambridge, MA (US)

(72) Inventors: Bernhardt Levy Trout, Lexington, MA (US); Curtiss Paul Schneider, Melrose, MA (US); Neeraj Jagdish Agrawal, Thousand Oaks, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/431,805

(22) PCT Filed: Sep. 27, 2013

(86) PCT No.: PCT/US2013/062108
§ 371 (c)(1),
(2) Date: Mar. 27, 2015

(87) PCT Pub. No.: WO2014/052713
PCT Pub. Date: Apr. 3, 2014

(65) Prior Publication Data
US 2015/0259435 A1    Sep. 17, 2015

Related U.S. Application Data

(60) Provisional application No. 61/830,829, filed on Jun. 4, 2013, provisional application No. 61/706,240, filed on Sep. 27, 2012.

(51) Int. Cl.
| C07K 16/22 | (2006.01) |
| C07K 16/30 | (2006.01) |
| A61K 39/395 | (2006.01) |
| C07K 16/32 | (2006.01) |

(52) U.S. Cl.
CPC .... *C07K 16/3015* (2013.01); *A61K 39/39591* (2013.01); *C07K 16/22* (2013.01); *C07K 16/32* (2013.01)

(58) Field of Classification Search
None
See application file for complete search history.

(56) References Cited

U.S. PATENT DOCUMENTS

| 5,736,137 | A | 4/1998 | Anderson et al. |
| 7,435,797 | B2 | 10/2008 | Lowman et al. |
| 7,799,900 | B2 | 9/2010 | Adams et al. |
| 8,147,832 | B2 | 4/2012 | Carr et al. |
| 2005/0069545 | A1 | 3/2005 | Carr et al. |
| 2005/0244403 | A1 | 11/2005 | Lazar et al. |
| 2006/0034835 | A1 | 2/2006 | Adams et al. |
| 2006/0121028 | A1 | 6/2006 | Reff |
| 2006/0234340 | A1 | 10/2006 | Vind |
| 2007/0092940 | A1 | 4/2007 | Eigenbrot et al. |
| 2007/0172475 | A1 | 7/2007 | Matheus et al. |
| 2008/0089885 | A1 | 4/2008 | Smith et al. |
| 2008/0299115 | A1 | 12/2008 | Lowman et al. |
| 2010/0034738 | A1 | 2/2010 | Goldenberg et al. |
| 2010/0322931 | A1 | 12/2010 | Harding et al. |
| 2011/0044977 | A1 | 2/2011 | Adler et al. |
| 2011/0076273 | A1 | 3/2011 | Adler et al. |
| 2011/0117110 | A1 | 5/2011 | Akamatsu et al. |
| 2011/0177074 | A1 | 7/2011 | Sivakumar et al. |
| 2011/0177095 | A1 | 7/2011 | Harding et al. |
| 2011/0182888 | A1* | 7/2011 | Ordentlich ........... A61K 31/138 424/133.1 |
| 2011/0257104 | A1 | 10/2011 | Chennamsetty et al. |
| 2012/0003211 | A1 | 1/2012 | Chennamsetty et al. |
| 2013/0209465 | A1* | 8/2013 | Jezek ............... A61K 39/39591 424/134.1 |

FOREIGN PATENT DOCUMENTS

| WO | WO 03/102132 A2 | 12/2003 |
| WO | WO 2005/092925 A2 | 10/2005 |
| WO | WO 2006/031370 A2 | 3/2006 |
| WO | WO 2006/113665 A2 | 10/2006 |
| WO | WO 2008/140603 A1 | 11/2008 |
| WO | WO 2009/155513 A2 | 12/2009 |
| WO | WO 2010/054007 A1 | 5/2010 |
| WO | WO 2011/116387 A1 | 9/2011 |
| WO | WO 2012/006596 A2 | 1/2012 |
| WO | WO 2012/020059 A1 | 2/2012 |
| WO | WO 2014/177771 A1 | 11/2014 |

OTHER PUBLICATIONS

Paul, Fundamental Immunology, 3rd Edition, 1993, pp. 292-295.*
Portolano et Al., Journal of Immunology, 1993, 150(3): 880-887.*
Trout, Follow-on biologics with enhanced stability. MIT. Nov. 15, 2012.
Wang et al., Potential aggregation prone regions in biotherapeutics: A survey of commercial monoclonal antibodies. MAbs. May-Jun. 2009;1(3):254-67. Epub May 29, 2009.
Courtois et al., Rational design of therapeutic mAbs against aggregation through protein engineering and incorporation of glycosylation motifs applied to bevacizumab. MAbs. 2016;8(1):99-112. doi:10.1080/19420862.2015.1112477.
Kayser et al., Glycosylation influences on the aggregation propensity of therapeutic monoclonal antibodies. Biotechnol J. Jan. 2011;6(1):38-44. doi: 10.1002/biot.201000091.

* cited by examiner

*Primary Examiner* — Hong Sang
(74) *Attorney, Agent, or Firm* — Wolf, Greenfield & Sacks, P.C.

(57) ABSTRACT

The invention provides HER2-binding proteins and VEGF-A-binding proteins having a reduced tendency to aggregate. Compositions and methods of use are also provided.

15 Claims, 1 Drawing Sheet

SEQUENCE LISTING

```
<160> NUMBER OF SEQ ID NOS: 52

<210> SEQ ID NO 1
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 2
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro
```

<210> SEQ ID NO 3
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 3

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 4
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Ser Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 5

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Ser Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro
    210             215             220
```

<210> SEQ ID NO 6
<211> LENGTH: 214
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (154)..(154)
<223> OTHER INFORMATION: Xaa can be any naturally occurring amino acid

<400> SEQUENCE: 6

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Xaa Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 220
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (177)..(177)
<223> OTHER INFORMATION: Xaa can be any naturally occurring amino acid

<400> SEQUENCE: 7

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Xaa Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro
            210                 215                 220

<210> SEQ ID NO 8
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 8

Asp Ile Gln Met Thr Gln Ser Pro Ser Ser Leu Ser Ala Ser Val Gly
 1               5                  10                  15
Asp Arg Val Thr Ile Thr Cys Ser Ala Ser Gln Asp Ile Ser Asn Tyr
             20                  25                  30
Leu Asn Trp Tyr Gln Gln Lys Pro Gly Lys Ala Pro Lys Val Leu Ile
         35                  40                  45
Tyr Phe Thr Ser Ser Leu His Ser Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Ser Thr Val Pro Trp
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 9
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

<210> SEQ ID NO 10
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 10

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

```
Ser His Glu Asp Pro Glu Val Lys Phe Asn Trp Tyr Val Asp Gly Val
 50                  55                  60

Glu Val His Asn Ala Lys Thr Lys Pro Arg Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 11
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 11

Asp Ile Gln Met Thr Gln Ser Pro Ser Ser Leu Ser Ala Ser Val Gly
1               5                  10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Asp Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 12
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Ser Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

<210> SEQ ID NO 13
<211> LENGTH: 213
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (154)..(154)
<223> OTHER INFORMATION: Xaa can be any naturally occurring amino acid

<400> SEQUENCE: 13

Asp Ile Gln Met Thr Gln Ser Pro Ser Ser Leu Ser Ala Ser Val Gly
1               5                   10                  15
```

```
Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Xaa Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 14
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (180)..(180)
<223> OTHER INFORMATION: Xaa can be any naturally occurring amino acid

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140
```

```
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Xaa Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
        210                 215                 220
```

<210> SEQ ID NO 15
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 15

```
Pro Lys Ser Cys Asp Lys Thr His Thr Cys Pro Pro Cys Pro Ala Pro
1               5                   10                  15

Glu Leu Lys Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 16
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 16

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Lys Ser Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230
```

<210> SEQ ID NO 17
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 17

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
            35                  40                  45

Asp Val Ser His Glu Asp Pro Glu Lys Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
```

```
                115                 120                 125
Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 18
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 18

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Lys His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

```
<210> SEQ ID NO 19
<211> LENGTH: 231
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (19)..(19)
<223> OTHER INFORMATION: Xaa can be any naturally occurring amino acid

<400> SEQUENCE: 19

Pro Lys Ser Cys Asp Lys Thr His Thr Cys Pro Pro Cys Pro Ala Pro
1               5                   10                  15

Glu Leu Xaa Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 20
<211> LENGTH: 231
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (37)..(37)
<223> OTHER INFORMATION: Xaa can be any naturally occurring amino acid

<400> SEQUENCE: 20

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Xaa Ser Arg Thr Pro Glu Val Thr Cys Val Val Val
```

```
                35                  40                  45
Asp Val Ser His Glu Asp Pro Glu Val Lys Phe Asn Trp Tyr Val Asp
 50                  55                  60

Gly Val Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 21
<211> LENGTH: 231
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (66)..(66)
<223> OTHER INFORMATION: Xaa can be any naturally occurring amino acid

<400> SEQUENCE: 21

Pro Lys Ser Cys Asp Lys Thr His Thr Cys Pro Pro Cys Pro Ala Pro
 1               5                  10                  15

Glu Leu Leu Gly Gly Pro Ser Val Phe Leu Phe Pro Pro Lys Pro Lys
                 20                  25                  30

Asp Thr Leu Met Ile Ser Arg Thr Pro Glu Val Thr Cys Val Val Val
            35                  40                  45

Asp Val Ser His Glu Asp Pro Glu Val Lys Phe Asn Trp Tyr Val Asp
 50                  55                  60

Gly Xaa Glu Val His Asn Ala Lys Thr Lys Pro Arg Glu Glu Gln Tyr
 65                  70                  75                  80

Asn Ser Thr Tyr Arg Val Val Ser Val Leu Thr Val Leu His Gln Asp
                 85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140
```

```
Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230
```

<210> SEQ ID NO 22
<211> LENGTH: 231
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (93)..(93)
<223> OTHER INFORMATION: Xaa can be any naturally occurring amino acid

<400> SEQUENCE: 22

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Xaa His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
210                 215                 220

Leu Ser Leu Ser Pro Gly Lys
225                 230
```

<210> SEQ ID NO 23

```
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 23

Ser Cys Asp Lys Thr His Thr Cys Pro Pro Cys Pro Ala Pro Glu Leu
1               5                   10                  15

Lys Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 24
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 24

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Lys Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
```

```
                        85                  90                  95
Asn Gly Lys Glu Tyr Lys Cys Lys Val Ser Asn Lys Ala Leu Pro Ala
                100                 105                 110
Pro Ile Glu Lys Thr Ile Ser Lys Ala Lys Gly Gln Pro Arg Glu Pro
            115                 120                 125
Gln Val Tyr Thr Leu Pro Pro Ser Arg Asp Glu Leu Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
                180                 185                 190
Thr Val Asp Lys Ser Arg Trp Gln Gln Gly Asn Val Phe Ser Cys Ser
            195                 200                 205
Val Met His Glu Ala Leu His Asn His Tyr Thr Gln Lys Ser Leu Ser
        210                 215                 220
Leu Ser Pro Gly Lys
225

<210> SEQ ID NO 25
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 25

Ser Cys Asp Lys Thr His Thr Cys Pro Pro Cys Pro Ala Pro Glu Leu
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
            35                  40                  45
Ser His Glu Asp Pro Glu Val Lys Phe Asn Trp Tyr Val Asp Gly Lys
        50                  55                  60
Glu Val His Asn Ala Lys Thr Lys Pro Arg Glu Glu Gln Tyr Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Ala Leu Pro Ala
                100                 105                 110
Pro Ile Glu Lys Thr Ile Ser Lys Ala Lys Gly Gln Pro Arg Glu Pro
            115                 120                 125
Gln Val Tyr Thr Leu Pro Pro Ser Arg Asp Glu Leu Thr Lys Asn Gln
        130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Lys Leu
                180                 185                 190
Thr Val Asp Lys Ser Arg Trp Gln Gln Gly Asn Val Phe Ser Cys Ser
            195                 200                 205
Val Met His Glu Ala Leu His Asn His Tyr Thr Gln Lys Ser Leu Ser
```

Leu Ser Pro Gly Lys
225

<210> SEQ ID NO 26
<211> LENGTH: 229
<212> TYPE: PRT
<213> ORGANISM: Artificial Sequence
<220> FEATURE:
<223> OTHER INFORMATION: Synthetic polypeptide

<400> SEQUENCE: 26

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Lys His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 27
<211> LENGTH: 229
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (17)..(17)
<223> OTHER INFORMATION: Xaa can be any naturally occurring amino acid

<400> SEQUENCE: 27

Ser Cys Asp Lys Thr His Thr Cys Pro Pro Cys Pro Ala Pro Glu Leu
1               5                   10                  15

Xaa Gly Gly Pro Ser Val Phe Leu Phe Pro Pro Lys Pro Lys Asp Thr
            20                  25                  30

```
Leu Met Ile Ser Arg Thr Pro Glu Val Thr Cys Val Val Asp Val
         35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 28
<211> LENGTH: 229
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (35)..(35)
<223> OTHER INFORMATION: Xaa can be any naturally occurring amino acid

<400> SEQUENCE: 28

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Xaa Ser Arg Thr Pro Glu Val Thr Cys Val Val Val Asp Val
        35                  40                  45

Ser His Glu Asp Pro Glu Val Lys Phe Asn Trp Tyr Val Asp Gly Val
 50                  55                  60

Glu Val His Asn Ala Lys Thr Lys Pro Arg Glu Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
```

```
                130              135              140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
        210                 215                 220

Leu Ser Pro Gly Lys
225

<210> SEQ ID NO 29
<211> LENGTH: 229
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (64)..(64)
<223> OTHER INFORMATION: Xaa can be any naturally occurring amino acid

<400> SEQUENCE: 29

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Xaa
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225
```

```
<210> SEQ ID NO 30
<211> LENGTH: 229
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (91)..(91)
<223> OTHER INFORMATION: Xaa can be any naturally occurring amino acid

<400> SEQUENCE: 30

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Xaa His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys
225

<210> SEQ ID NO 31
<211> LENGTH: 1255
<212> TYPE: PRT
<213> ORGANISM: Artificial Sequence
<220> FEATURE:
<223> OTHER INFORMATION: Synthetic polypeptide

<400> SEQUENCE: 31

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
```

```
            50                  55                  60
Leu Pro Thr Asn Ala Ser Leu Ser Phe Leu Gln Asp Ile Gln Glu Val
 65                  70                  75                  80

Gln Gly Tyr Val Leu Ile Ala His Asn Gln Val Arg Gln Val Pro Leu
                 85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480
```

```
Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
            645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895
```

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
    915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 32
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 32

```
Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
                20                  25                  30
Gly Gly Gln Asn His His Glu Val Val Lys Phe Met Asp Val Tyr Gln
            35                  40                  45
Arg Ser Tyr Cys His Pro Ile Glu Thr Leu Val Asp Ile Phe Gln Glu
        50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Lys Lys Ser Val
    130                 135                 140
Arg Gly Lys Gly Lys Gly Gln Lys Arg Lys Arg Lys Lys Ser Arg Tyr
145                 150                 155                 160
Lys Ser Trp Ser Val Tyr Val Gly Ala Arg Cys Cys Leu Met Pro Trp
                165                 170                 175
Ser Leu Pro Gly Pro His Pro Cys Gly Pro Cys Ser Glu Arg Arg Lys
            180                 185                 190
His Leu Phe Val Gln Asp Pro Gln Thr Cys Lys Cys Ser Cys Lys Asn
        195                 200                 205
Thr Asp Ser Arg Cys Lys Ala Arg Gln Leu Glu Leu Asn Glu Arg Thr
    210                 215                 220
Cys Arg Cys Asp Lys Pro Arg Arg
225                 230
```

<210> SEQ ID NO 33
<211> LENGTH: 716
<212> TYPE: DNA
<213> ORGANISM: Artificial Sequence
<220> FEATURE:
<223> OTHER INFORMATION: Synthetic polynucleotide

<400> SEQUENCE: 33

```
gtcgacatgg gttggagcct catcttgctc ttccttgtcg ctgttgctac gcgtgtcctg      60
tccgacatcc agatgactca gagcccaagc agcttgtctg caagcgtggg cgaccgagtg     120
acaatcacct gtagggcctc acaggacgtg aacaccgctg tggcctggta tcaacagaag     180
cccggcaagg cccccaaact gcttatctat agcgccagct tcctgtatag cggcgtgccc     240
tctaggttca gcggctcaag gagcggcacg gattttacct tgaccatctc ttccctgcag     300
cccgaagact cgccacttta ctactgccag cagcactaca ccactccccc taccttcggc     360
caaggcacga aagtggagat caagaggact gttgcagcgc cagcgtttt catctttccg      420
cccagtgacg agcagctgaa gtctggcacg gcctccgtgg tgtgcctgct gaacaacttc     480
tacccgaggg aggcgaaggt ccaatggaag gtggacaacg ccctgcaatc ggcaacagc      540
caagagagcg tgacggagca ggatagcaag acagcacgt acagcctgtc tagcaccctg     600
acgttgagca aggcggacta cgaaaagcac aaggtgtacg cctgcgaggt cacgcatcaa     660
```

```
ggtctgagca gccccgtgac caagagcttc aacaggggcg agtgctaagc ggccgc      716
```

<210> SEQ ID NO 34
<211> LENGTH: 1427
<212> TYPE: DNA
<213> ORGANISM: Artificial Sequence
<220> FEATURE:
<223> OTHER INFORMATION: Synthetic polynucleotide

<400> SEQUENCE: 34

```
gtcgacatgg gttggagcct catcttgctc ttccttgtcg ctgttgctac gcgtgtcctg    60
tccgaagtgc agttggtgga gagcggaggc ggcctggtcc agccgggagg cagcctgcga   120
ttgtcatgtg ctgcgagcgg tttcaacatc aaggacacgt atatccattg ggtcaggcaa   180
gctcctggga aaggcctcga gtgggtcgcc aggatctacc cgaccaacgg ctacaccagg   240
tacgccgaca gtgtgaaagg caggttcacc atcagcgccg ataccagcaa gaacacggcc   300
taccttcaga tgaactccct tcgcgcggaa gatacggcgg tttattactg ttcaagatgg   360
ggcggagacg gcttctacgc catggactac tggggccagg gcactctggt cacagtgtcc   420
agcgcgagca ccaaaggccc gagcgtcttc cctcttgccc ccagcagcaa atcaaccagc   480
ggtgggacag cggccctggg gtgcctggta aaagattact tccggagcc cgtgacggtg    540
tcctggaaca gtggggccct gacgagcggc gtgcatacct cccagccgt gcttcaaagc    600
agcgggctct actccctgag ctccgtagtg accgtcccta gtagtagcct gggcacccaa   660
acctacatct gcaacgtcaa ccataagccc agcaacacca aggttgacaa gaaggtggag   720
ccccccaagt catgcgacaa gacgcacacc tgtcccccat gcccggcacc cgagcttttg   780
ggagggccca gcgtgttcct gttccccccg aagcccaagg atactctgat gatcagccgc   840
accccggagg taacttgcgt ggtggtggat gtaagccacg aggacccgga agtgaagttc   900
aactggtacg tggacggcgt ggaggtgcac aacgccaaaa ctaagccgag agaggagcag   960
tataacagca cctacagggt ggtgtcagtc ctcacggtgc tgcaccaaga ctggctgaac  1020
ggcaaagagt acaagtgcaa ggtgagcaac aaagccctgc cagcgcccat cgagaagaca  1080
atcagcaagg ccaaaggaca gccccaggga accgcaggttt atacccctgcc ccctcccgc  1140
gacgagctta ccaagaacca ggtcagcctg acttgcctcg tcaagggggtt ttatcccagt  1200
gacatcgccg tcgaatggga gagcaacggc caacccgaga caactacaa gaccacgccc  1260
cctgtgcttg acagcgacgg atcattcttt ctgtacagca agctgaccgt ggacaaaagc  1320
cggtggcaac agggcaatgt gtttagctgt tctgtgatgc atgaggcgct tcacaaccat  1380
tacacccaga gagcctgtc tctgagtccc ggtaaataag cggccgc                 1427
```

<210> SEQ ID NO 35
<211> LENGTH: 716
<212> TYPE: DNA
<213> ORGANISM: Artificial Sequence
<220> FEATURE:
<223> OTHER INFORMATION: Synthetic polynucleotide

<400> SEQUENCE: 35

```
gtcgacatgg gttggagcct catcttgctc ttccttgtcg ctgttgctac gcgtgtcctg    60
tccgacatcc agatgaccca aagccccagc tctctgagcg cgagcgtggg cgacagggtg   120
acgatcacct gcagcgcaag ccaggacatc agcaactacc tcaactggta tcagcagaag   180
cccggcaagg ctcccaaggt cctgatctac ttcaccagca gcctccacag cggcgtaccc   240
```

```
agcaggttca gcggcagcgg ctctgggacc gatttcaccc tcaccatcag ctccctgcaa    300
cccgaagact tcgccaccta ctactgccaa cagtactcca ccgtgccctg gacctttggg    360
cagggaacca agtcgagat caagaggacc gtggctgcgc ccagcgtgtt cattttcccc    420
ccgagcgacg agcagctgaa gtccggcacc gccagcgtcg tgtgcctgct gaacaacttc    480
taccccaggg aagccaaggt gcagtggaag gtggacaacg ccctgcagag cggcaactcc    540
caggagagcg taaccgagca ggacagcaag gacagtacct acagcctgag cagcacactg    600
acccttagca aggccgacta cgagaagcac aaggtgtacg cctgcgaggt gacccatcag    660
ggtctgagct ctcccgtgac caagagcttc aacaggggcg agtgctgagc ggccgc    716

<210> SEQ ID NO 36
<211> LENGTH: 1433
<212> TYPE: DNA
<213> ORGANISM: Artificial Sequence
<220> FEATURE:
<223> OTHER INFORMATION: Synthetic polynucleotide

<400> SEQUENCE: 36
gtcgacatgg gttggagcct catcttgctc ttccttgtcg ctgttgctac gcgtgtcctg     60
tccgaggtgc aactcgtaga gagtggcggt gggctggtcc agccaggcgg ctcattgagg    120
ctttcatgtg ctgccagcgg ttacacgttc accaactatg gcatgaactg ggtcaggcag    180
gctcccggaa agggcctgga gtgggtgggg tggatcaata cgtacaccgg cgaaccgacc    240
tacgctgccg actttaagag aaggttcacc ttcagcctgg acaccagcaa gtcaaccgct    300
tacctgcaaa tgaacagtct gagggccgag gacacggcgg tctactactg cgccaagtac    360
ccccattact acgggagcag ccattggtac ttcgacgttt ggggccaggg cacgctggtc    420
acagtgagct ccgcctcaac gaaaggtccg tccgtcttcc ccctggctcc tagctctaag    480
agcacgtccg ggggaacggc tgcgctgggg tgcctggtaa aggattactt cccggagccc    540
gtcaccgtga gctggaacag cggtgcgctg acgagcggcg tgcacacatt tcctgccgtc    600
ctgcagtcct ccgggcttta ctccctcagc agcgtcgtga cggtcccaag cagcagcctt    660
ggcacacaga cctacatctg caacgtgaac cacaagccct ccaacacgaa ggtggacaag    720
aaagttgagc ccaagagctg cgataaaact cacacctgtc ccccgtgccc cgcacccgag    780
ctcctgggcg gaccgagcgt gttcctgttc ccgcctaagc cgaaagatac cctgatgatc    840
agccgaaccc ccgaggtcac atgcgtggtg gtggacgtga gccacgagga tcccgaagtg    900
aagttcaact ggtacgtgga cggcgtggag gtccacaacg ccaagacgaa accccgggag    960
gagcagtaca acagcaccta cagggtggtg agcgtgctga cagtgctgca tcaggactgg   1020
ttgaacggca aggagtacaa gtgcaaggtc agcaacaaag cactgcctgc cgcgatcgag   1080
aagaccatca gcaaggccaa gggccaaccc agggagcccc aggtgtatac ccttccgcca   1140
agccgggacg aattgacgaa gaaccaggtc tcacttactt gcctcgtcaa gggcttctac   1200
ccctccgaca tcgccgtgga atgggagagc aacgggcaac ccgagaacaa ctacaagacc   1260
accccgccag ttttggacag cgacggctct ttcttcctct acagcaagct gaccgttgac   1320
aagagcaggt ggcaacaggg aaacgtgttc agctgcagtg tgatgcacga ggccctgcac   1380
aaccactaca cccagaaatc actgtctctg tcacccggca agtgagcggc cgc           1433

<210> SEQ ID NO 37
<211> LENGTH: 220
<212> TYPE: PRT
<213> ORGANISM: Artificial Sequence
```

<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 37

Glu Val Gln Leu Xaa Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 38
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

```
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Lys Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 39
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 39

```
Glu Val Gln Leu Lys Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220
```

<210> SEQ ID NO 40
<211> LENGTH: 220

```
<212> TYPE: PRT
<213> ORGANISM: Artificial Sequence
<220> FEATURE:
<223> OTHER INFORMATION: Synthetic polypeptide

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Lys Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220

<210> SEQ ID NO 41
<211> LENGTH: 213
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (50)..(50)
<223> OTHER INFORMATION: Xaa can be any naturally occurring amino acid

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Xaa Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
```

Thr Phe Gly Gln Gly Thr Lys Val Glu Ile Lys Arg Thr Val Ala Ala
                85                  90                  95
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu
            210

<210> SEQ ID NO 42
<211> LENGTH: 213
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (110)..(110)
<223> OTHER INFORMATION: Xaa can be any naturally occurring amino acid

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Xaa Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu
    210

<210> SEQ ID NO 43
<211> LENGTH: 213
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (201)..(201)
<223> OTHER INFORMATION: Xaa can be any naturally occurring amino acid

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Xaa Ser Ser Pro Val Thr Lys Ser
        195                 200                 205

Phe Asn Arg Gly Glu
    210

<210> SEQ ID NO 44
<211> LENGTH: 224
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 44

Glu Val Gln Leu Xaa Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

```
Gly Met Asn Trp Val Arg Gln Ala Pro Gly Lys Gly Leu Glu Trp Val
         35                  40                  45

Gly Trp Ile Asn Thr Tyr Thr Gly Glu Pro Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

<210> SEQ ID NO 45
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 45

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
             20                  25                  30

Leu Asn Trp Tyr Gln Gln Lys Pro Gly Lys Ala Pro Lys Val Leu Ile
         35                  40                  45

Tyr Asp Thr Ser Ser Leu His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 46
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Lys Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 47
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

```
Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Lys Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu
    210
```

<210> SEQ ID NO 48
<211> LENGTH: 213
<212> TYPE: PRT
<213> ORGANISM: Artificial Sequence
<220> FEATURE:
<223> OTHER INFORMATION: Synthetic polypeptide

<400> SEQUENCE: 48

```
Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
         35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

Ala Cys Glu Val Thr His Gln Gly Lys Ser Ser Pro Val Thr Lys Ser
            195                 200                 205

Phe Asn Arg Gly Glu
    210

<210> SEQ ID NO 49
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 49

Glu Val Gln Leu Lys Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

<210> SEQ ID NO 50
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe

```
            50                  55                  60
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Lys Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220
```

```
<210> SEQ ID NO 51
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 51

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Asn Val Thr His Gln Gly Leu Ser Ser Pro Val Thr Lys Ser
```

```
                195                 200                 205
Phe Asn Arg Gly Glu Cys
    210

<210> SEQ ID NO 52
<211> LENGTH: 220
<212> TYPE: PRT
<213> ORGANISM: Artificial Sequence
<220> FEATURE:
<223> OTHER INFORMATION: Synthetic polypeptide

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Asn Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro
    210                 215                 220
```

US 9,777,067 B2

HER2- AND VEGF-A-BINDING PROTEINS WITH ENHANCED STABILITY

RELATED APPLICATIONS

This application is a national stage filing under 35 U.S.C. §371 of international application number PCT/US2013/062108, filed Sep. 27, 2013, which was published under PCT Article 21(2) in English and claims the benefit under 35 U.S.C. §119(e) of U.S. provisional application Nos. 61/830,829, filed Jun. 4, 2013, and 61/706,240, filed Sep. 27, 2012, the entire contents of each of which are incorporated by reference herein.

SEQUENCE LISTING

The sequence listing filed on May 23, 2017, entitled "M065670258US02-SEQ-HJD" and having a size of 111 KB, is hereby incorporated by reference in its entirety.

FIELD OF THE INVENTION

Aspects of the invention relate to proteins that are less prone to aggregation as compared to existing proteins and that may be suitable for preparing highly concentrated protein compositions.

BACKGROUND OF INVENTION

Many therapeutic proteins such as, for example, antibodies require administration by injection or infusion via the intravenous route. The amount of protein that can be administered intravenously is limited by solubility and stability of the protein in a suitable liquid composition and by the volume of the infusion fluid. An alternative administration pathway is subcutaneous injection. This injection pathway requires a high protein concentration in the final solution to be injected (Shire et al., *Journal of Pharmaceutical Science*, 2004; 93(6): 1390-1402; Roskos et al., *Drug Development Research*, 2004; 61(3): 108-120). Achieving the high protein concentration necessary for subcutaneous delivery can be problematic due to protein aggregation. Aggregation is the result of intermolecular interactions and, thus, is enhanced by high protein concentrations. The presence of protein aggregates in an injected solution, even in small doses, poses a threat of an immune response that can reduce the efficacy of the protein over time and, more importantly, has the potential to elicit adverse reactions (Frokjaer, S. et al., *Nature Reviews Drug Discovery*, 2005; 4(4): 298-306; Wang, W., et al., *International Journal of Pharmaceutics*, 2005; 289: 1-30; Manning, M. C., et al., *Pharmaceutical Research*, 2010; 27(4): 544-575; Cromwell, M. E. M., et al., 2006; Rosenberg, A. S., *AAPS J.*, 2006; 8(3): E501-E507).

SUMMARY OF INVENTION

The invention provides, inter alia, proteins that are less prone to aggregation as compared to existing proteins. The invention is based, in part, on the surprising discovery that specific mutations at particular amino acids in Human Epidermal Growth Factor Receptor 2 (HER2)-binding proteins and in Vascular Endothelial Growth Factor A (VEGF-A)-binding proteins can reduce the tendency of the proteins to aggregate in solution.

Thus, in various aspects and embodiments of the invention, provided herein are HER2-binding proteins comprising a light chain domain having an amino acid sequence of SEQ ID NO:1 modified to include an amino acid substitution of a negative polar amino acid at $L_{154}$ or a positive polar amino acid at $L_{154}$; and/or a heavy chain domain having an amino acid sequence of SEQ ID NO:2 modified to include at least one amino acid substitution selected from a positive polar amino acid at $V_5$, a neutral polar amino acid at $L_{177}$, and a positive polar amino acid at $L_{177}$; and/or an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$. Also provided herein are compositions comprising the HER2-binding proteins of the invention and methods of use. Non-limiting examples of HER2-binding protein amino acid substitutions contemplated by the invention are presented in Table I.

TABLE I

Examples of HER2-binding protein amino acid substitutions.

| Full length, wild type sequence | Contemplated substitutions |
| --- | --- |
| light chain domain (SEQ ID NO: 1) | L154 (SEQ ID NO: 6) - substitution to a negative polar amino acid or a positive polar amino acid<br>L154D (SEQ ID NO: 4)<br>L154K (SEQ ID NO: 38)<br>E195N (SEQ ID NO: 51) |
| Fab heavy chain domain (SEQ ID NO: 2) | V5 (SEQ ID NO: 37) - substitution to a positive polar amino acid<br>V5K (SEQ ID NO: 39)<br>L177 (SEQ ID NO: 7) - substitution to a neutral polar amino acid or a positive polar amino acid<br>L177S (SEQ ID NO: 5)<br>L177K (SEQ ID NO: 40)<br>L115N (SEQ ID NO: 52) |
| Fc domain (SEQ ID NO: 3) | L19 (SEQ ID NO: 19) - substitution to a positive polar amino acid<br>L19K (SEQ ID NO: 15)<br>I37 (SEQ ID NO: 20) - substitution to a positive polar amino acid<br>I37K (SEQ ID NO: 16)<br>V66 (SEQ ID NO: 21) - substitution to a positive polar amino acid<br>V66K (SEQ ID NO: 17)<br>L93 (SEQ ID NO: 22) - substitution to a positive polar amino acid<br>L93K (SEQ ID NO: 18) |

In some embodiments, the HER2-binding proteins comprise a light chain domain having an amino acid sequence of SEQ ID NO:1 modified to include at least one amino acid substitutions, one of which is a negative polar amino acid at $L_{154}$ or a positive polar amino acid at $L_{154}$; and/or a heavy chain domain of SEQ ID NO:2 modified to include at least two amino acid substitutions, one of which is selected from a positive polar amino acid at $V_5$, a neutral polar amino acid at $L_{177}$, and a positive polar amino acid at $L_{177}$; and/or an Fc domain of SEQ ID NO:3 modified to include at least two amino acid substitutions, one of which is selected from a positive polar amino acid at position $L_{19}$, a positive polar amino acid at position $I_{37}$, a positive polar amino acid at position $V_{66}$, and a positive polar amino acid at position $L_{93}$.

In some embodiments, the HER2-binding proteins comprise a light chain domain having an amino acid sequence of SEQ ID NO:1 modified to include at least one amino acid substitution that is a negative polar amino acid at $L_{154}$ or a positive polar amino acid at $L_{154}$; and/or a heavy chain domain of SEQ ID NO:2 modified to include at least two amino acid substitutions, one of which is a positive polar amino acid at $V_5$ and one of which is selected from a neutral polar amino acid at $L_{177}$ and a positive polar amino acid at $L_{177}$; and/or an Fc domain of SEQ ID NO:3 modified to include at least one, at least two, at least three or at least four amino acid substitutions, one of which is a positive polar amino acid at position $L_{19}$, one of which is a positive polar amino acid at position $I_{37}$, one of which is a positive polar amino acid at position $V_{66}$, and one of which is a positive polar amino acid at position $L_{93}$.

In some embodiments, the negative polar amino acid at $L_{154}$ of SEQ ID NO:1 is aspartic acid (D) or glutamic acid (E). In some embodiments, the neutral polar amino acid at $L_{177}$ of SEQ ID NO:2 is selected from asparagine (N), cysteine (C), glutamine (Q), histidine (H), serine (S), threonine (T) and tyrosine (Y). In some embodiments, the positive polar amino acid at $L_{154}$ of SEQ ID NO: 1, at $V_5$ and/or $L_{177}$ of SEQ ID NO:2, and/or at $L_{19}$, $I_{37}$, $V_{66}$ and/or $L_{93}$ of SEQ ID NO:3 is arginine (R) or lysine (K).

In some embodiments, the HER2-binding proteins comprise a light chain domain having an amino acid sequence of SEQ ID NO:1, a heavy chain domain having an amino acid sequence of SEQ ID NO:2, a human IgG Fc domain, or an Fc domain having an amino acid sequence of SEQ ID NO:3

In some embodiments, the HER2-binding proteins comprise a light chain domain having an amino acid sequence of SEQ ID NO:6, where position 154 is optionally modified to a negative polar or positive polar amino acid (e.g., D or K). In some embodiments, the HER2-binding proteins comprise a heavy chain domain having an amino acid sequence of SEQ ID NO:7, where position 177 is optionally modified to a neutral polar or positive polar amino acid (e.g., S or K). In some embodiments, the HER2-binding proteins comprise a heavy chain domain having an amino acid sequence of SEQ ID NO:37, where position 5 is optionally modified to a positive polar amino acid (e.g., K). In some embodiments, the HER2-binding proteins comprise an Fc domain having an amino acid sequence of SEQ ID NO:19, SEQ ID NO:20, SEQ ID NO:21, or SEQ ID NO:22, where any combination of position 19 of SEQ ID NO:19, position 37 of SEQ ID NO:20, position 66 of SEQ ID NO:21 or position 93 of SEQ ID NO:22 is optionally modified to a positive polar amino acid (e.g., K).

In some aspects of the invention, provided herein are HER2-binding proteins comprising a light chain domain having an amino acid sequence of SEQ ID NO:1 modified to include an acid substitution of $L_{154}$D or $L_{154}$K, and/or a heavy chain domain having an amino acid sequence of SEQ ID NO:2 modified to include at least one amino acid substitution selected from $V_5$K, $L_{177}$S and $L_{177}$K, and/or an Fc domain having an amino acid sequence of SEQ ID NO:3 modified to include at least one amino acid substitution selected from $L_{19}$K, $I_{37}$K, $V_{66}$K and $L_{93}$K.

In some embodiments, the HER2-binding proteins comprise a light chain domain having an amino acid sequence of SEQ ID NO:4, SEQ ID NO:38 or SEQ ID NO:51. In some embodiments, the HER2-binding proteins comprise a heavy chain domain having an amino acid sequence of SEQ ID NO:5, SEQ ID NO:39, SEQ ID NO:40 or SEQ ID NO:52. In some embodiments, the HER2-binding proteins comprise an Fc domain having an amino acid sequence of SEQ ID NO:15, SEQ ID NO:16, SEQ ID NO:17, or SEQ ID NO:18.

In some embodiments, the HER2-binding proteins comprise a light chain domain having an amino acid sequence of SEQ ID NO:1 modified to include an amino acid substitution of a negative polar amino acid at $L_{154}$ or a positive polar amino acid at $L_{154}$, and a heavy chain domain having an amino acid sequence of SEQ ID NO:2. In some embodiments, the negative polar amino acid at $L_{154}$ of SEQ ID NO:1 may be D or E or the positive polar amino acid at $L_{154}$ may be R or K. In some embodiments, the HER2-binding proteins comprise a light chain domain having an amino acid sequence of SEQ ID NO:1, and a heavy chain domain having an amino acid sequence of SEQ ID NO:2 modified to include at least one amino acid substitution selected from a positive polar amino acid at $V_5$, a neutral polar amino acid at $L_{177}$, and a positive polar amino acid at $L_{177}$. In some embodiments, the neutral polar amino acid at $L_{177}$ of SEQ ID NO:2 is selected from N, C, Q, H, S, T and Y. In some embodiments, the positive polar amino acid at $V_5$ and/or at $L_{177}$ of SEQ ID NO:2 is R or K.

In some embodiments, the HER2-binding proteins comprise a human IgG1 Fc domain. In some embodiments, the HER2-binding proteins comprise an Fc domain having an amino acid sequence of SEQ ID NO:3. In some embodiments, the Fc domain having the amino acid sequence of SEQ ID NO:3 is modified to include at least one amino acid substitution selected from $L_{19}$, $I_{37}$, $V_{66}$ and $L_{93}$. In some embodiments, the Fc domain having the amino acid sequence of SEQ ID NO:3 is modified to include at least one amino acid substitution selected from $L_{19}$K, $I_{37}$K, $V_{66}$K and $L_{93}$K.

In some aspects of the invention, provided herein are HER2-binding proteins comprising an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$. In some embodiments, the positive polar amino acid is arginine (R) or lysine (K). In some embodiments, the HER2-binding proteins comprise an Fc domain having an amino acid sequence of SEQ ID NO:3 modified to include at least one amino acid substitution selected from $L_{19}$K, $I_{37}$K, $V_{66}$K and $L_{93}$K.

In some embodiments, the HER2-binding proteins comprise an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$; a light chain domain having an amino acid sequence of SEQ ID NO:1; and a heavy chain domain having an amino acid sequence of SEQ ID NO:2.

In some embodiments, the HER2-binding proteins comprise an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$; a light chain domain having an amino acid sequence of SEQ ID NO:1 modified to include an amino acid substitution of a negative polar amino acid at $L_{154}$ or a positive polar amino acid at $L_{154}$; and a heavy chain domain having an amino acid sequence of SEQ ID NO:2. In some embodiments, the HER2-binding proteins comprise an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$; a light chain domain having an amino acid sequence of SEQ ID NO:1; and heavy chain domain having an amino acid sequence of SEQ ID NO:2 modified to include at least one amino acid substitution selected from a positive polar amino acid at $V_5$, a neutral polar amino acid at $L_{177}$, and a positive polar amino acid at $L_{177}$.

In some embodiments, the HER2-binding proteins are in the form of monoclonal antibodies such as, for example, chimeric monoclonal antibodies or humanized monoclonal antibodies. In some embodiments, the HER2-binding proteins are in the form of antigen-binding antibody fragments such as, for example, Fab antibody fragments. In some embodiments, the HER2-binding proteins are in the form of antibody-like proteins such as, for example, fusion proteins, single-chain Fv antibody fragments, and/or minibodies. In some embodiments, the HER2-binding proteins are conjugated to a therapeutic or diagnostic agent such as a toxin and/or a radioisotope.

In some embodiments, the HER2-binding proteins are lyophilized. In some embodiments, the HER2-binding proteins are in solution.

In some aspects of the invention, provided herein are compositions comprising any of the HER2-binding proteins of the invention. In some embodiments, the compositions comprise HER2-binding proteins comprising a light chain domain having an amino acid sequence of SEQ ID NO:1 modified to include an amino acid substitution of a negative polar amino acid at $L_{154}$ or a positive polar amino acid at $L_{154}$; and/or a heavy chain domain having an amino acid sequence of SEQ ID NO:2 modified to include at least one amino acid substitution selected from a positive polar amino acid at $V_5$, a neutral polar amino acid at $L_{177}$, and a positive polar amino acid at $L_{177}$. In some embodiments, the compositions comprise HER2-binding proteins comprising a light chain domain having an amino acid sequence of SEQ ID NO:1 modified to include an amino acid substitution of $L_{154}D$ or $L_{154}K$; and/or a heavy chain domain having an amino acid sequence of SEQ ID NO:2 modified to include at least one amino acid substitution selected from $V_5K$, $L_{177}S$ and $L_{177}K$. In some embodiments, the compositions comprise HER2-binding proteins comprising an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$. In some embodiments, the compositions comprise HER2-binding proteins comprising an Fc domain having an amino acid sequence of SEQ ID NO:3 modified to include at least one amino acid substitution selected from $L_{19}K$, $I_{37}K$, $V_{66}K$ and $L_{93}K$.

In some embodiments, the HER2-binding proteins comprise a light chain domain having an amino acid sequence of SEQ ID NO:1 modified to include at least an amino acid substitution of $E_{195}N$.

In some embodiments, the HER2-binding proteins comprise a heavy chain domain having an amino acid sequence of SEQ ID NO:2 modified to include at least an amino acid substitution of $L_{115}N$.

In some aspects of the invention, provided herein are HER2-binding proteins comprising a light chain domain having an amino acid sequence of SEQ ID NO:1 modified to include an amino acid substitution of $E_{195}N$, and/or a heavy chain domain having an amino acid sequence of SEQ ID NO:2 modified to include an amino acid substitution of $L_{115}N$. In some embodiments, the HER2-binding proteins comprise a light chain domain having an amino acid sequence of SEQ ID NO:1 modified to include an amino acid substitution of $E_{195}N$, and a heavy chain domain having an amino acid sequence of SEQ ID NO:2. In some embodiments, the HER2-binding proteins comprise a light chain domain having an amino acid sequence of SEQ ID NO:1 and a heavy chain domain having an amino acid sequence of SEQ ID NO:2 modified to include an amino acid substitution of $L_{115}N$.

In some embodiments, the compositions comprise the HER2-binding proteins at a concentration of about 20 mg/ml to about 350 mg/ml. In some embodiments, the concentration of the HER2-binding proteins is about 100 mg/ml to about 250 mg/ml. In some embodiments, the concentration of the HER2-binding proteins is about 120 mg/ml to about 150 mg/ml. In some embodiments, the concentration of the HER2-binding proteins is about 120 mg/ml, about 130 mg/ml or about 140 mg/ml. In some embodiments, the concentration of the HER2-binding proteins is about 120 mg/ml or is 120 mg/ml.

In some embodiments, the compositions are liquid. In some embodiments, the compositions are formulated for subcutaneous injection and/or other non-intravenous delivery routes such as, for example, intramuscular injection.

In some embodiments, the compositions further comprise at least one buffer, at least one stabilizer and/or at least one surfactant. In some embodiments, the buffer is present at a concentration of about 1 mM to about 100 mM. In some embodiments, the buffer provides a pH of 5.5±2.0. In some embodiments, the stabilizer is present at a concentration of about 100 mM to about 500 mM. In some embodiments, a secondary stabilizer is present. In some embodiments, the secondary stabilizer is arginine, ornithine, lysine, histidine, glutamic acid, aspartic acid, isoleucine, leucine, alanine, phenylalanine, tyrosine, tryptophan, methionine, serine or proline (e.g., as a hydrochloride). In some embodiments, methionine is present at a concentration of about 5 mM to about 25 mM. In some embodiments, the surfactant is a nonionic surfactant. In some embodiments, the surfactant is present at a concentration of about 0.01% to about 0.1%. In some embodiments, the compositions further comprise at least one pharmaceutically acceptable carrier, excipient, and/or diluent. In some embodiments, the compositions further comprise additional agents (e.g., therapeutic agents). In some embodiments, the compositions are sterile.

In some embodiments, the compositions comprise the HER2-binding proteins, histidine HCl, trehalose dehydrate, methionine and/or polysorbate 80. In some embodiments, the compositions comprise about 100 mg/ml to about 150 mg/ml of the HER2-binding proteins, about 10 mM to about 30 mM histidine HCl, about 200 mM to about 220 mM trehalose dehydrate, about 5 mM to about 15 mM methionine and/or about 0.04% to about 0.08% polysorbate 80. In some embodiments, the compositions comprise about 120 mg/ml of the HER2-binding proteins, about 20 mM histidine HCl, about 210 mM trehalose dehydrate, about 10 mM methionine and/or about 0.06% polysorbate 80.

In some aspects of the invention, provided herein are methods of treating a condition in a subject in need thereof, comprising administering to the subject any of the HER2-binding proteins and/or compositions described herein. In some embodiments, the methods comprise administering to the subject a therapeutically effective amount of any of the HER2-binding proteins and/or compositions provided herein. In some embodiments, the condition is cancer or a non-malignant condition. In some embodiments, the condition involves HER2-expressing cells. In some embodiments, the cancer is a human cancer such as, for example, breast cancer, and other cancers expressing or overexpressing HER2.

In some aspects of the invention, provided herein are uses of the HER2-binding proteins for the preparation of a medicament for treating a condition amenable to treatment with a HER2-binding protein.

In some aspects of the invention, provided herein are nucleic acids encoding the HER2-binding proteins, vectors comprising the nucleic acids, expression cassettes comprising the nucleic acids, and host cells comprising the nucleic acids and/or vectors and/or expression cassettes. In some embodiments, the nucleic acids are isolated.

In some aspects of the invention, provided herein are methods of producing a HER2-binding protein (e.g., an anti-HER2 antibody), the methods comprising culturing any of the host cells described herein to produce the HER2-binding protein. In certain embodiments, the methods include an additional step of isolating the HER2-binding protein.

In some aspects of the invention, provided herein are kits comprising a container and any of the HER2-binding proteins and/or compositions contained therein. In some embodiments, the kits further comprise instructions for using the kits. In some embodiments, the kits further comprise a package insert or label indicating that the kits can be used to treat cancer or a non-malignant condition such as, for example, one characterized by the overexpression of HER2. In some embodiments, the kits comprise injection components such as, for example, a syringe or a syringe filled with the HER2-binding proteins or a composition containing the HER2-binding proteins. In some embodiments, the volume of the composition in the kits is about 2 ml. In some embodiments, the volume of the composition is less than 2 ml. In some embodiments, the concentration of the HER2-binding proteins in about 2 ml or less of a composition is about 100 mg/ml to about 150 mg/ml. In some embodiments, the concentration of the HER2-binding proteins is about 120 mg/ml or is 120 mg/ml.

In various other aspects the invention, provided herein are Vascular Endothelial Growth Factor A (VEGF-A)-binding proteins comprising a light chain domain having an amino acid sequence of SEQ ID NO:8 modified to include at least one amino acid substitution selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$, and/or a heavy chain domain having an amino acid sequence of SEQ ID NO:9 modified to include at least one amino acid substitution selected from a positive polar amino acid at $V_5$, a neutral polar amino acid at $L_{180}$, and a positive polar amino acid at $L_{180}$, and/or an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$. Also provided herein are compositions comprising the VEGF-A-binding proteins and methods of use. Non-limiting examples of VEGF-A-binding protein amino acid substitutions contemplated by the invention are presented in Table II.

TABLE II

Examples of VEGF-A-binding protein amino acid substitutions.

| Full length, wild type sequence | Contemplated substitutions |
| --- | --- |
| light chain domain (SEQ ID NO: 8) | F50 (SEQ ID NO: 41) - substitution to a negative polar amino acid<br>F50D (SEQ ID NO: 45)<br>V110 (SEQ ID NO: 42) - substitution to a positive polar amino acid<br>V110K (SEQ ID NO: 46)<br>L154 (SEQ ID NO: 13) - substitution to a negative polar amino acid or a positive polar amino acid<br>L154D (SEQ ID NO: 11)<br>L154K (SEQ ID NO: 47)<br>L201 (SEQ ID NO: 43) - substitution to a positive polar amino acid<br>L201K (SEQ ID NO: 48) |
| Fab heavy chain domain (SEQ ID NO: 9) | V5 (SEQ ID NO: 44) - substitution to a positive polar amino acid<br>V5K (SEQ ID NO: 49)<br>L180 (SEQ ID NO: 14) - substitution to a neutral polar amino acid or a positive polar amino acid<br>L180S (SEQ ID NO: 12)<br>L180K (SEQ ID NO: 50) |
| Fc domain (SEQ ID NO: 10) | L17 (SEQ ID NO: 27) - substitution to a positive polar amino acid<br>L17K (SEQ ID NO: 23)<br>I35 (SEQ ID NO: 28) - substitution to a positive polar amino acid<br>I35K (SEQ ID NO: 24)<br>V64 (SEQ ID NO: 29) - substitution to a positive polar amino acid<br>V64K (SEQ ID NO: 25)<br>L91 (SEQ ID NO: 30) - substitution to a positive polar amino acid<br>L91K (SEQ ID NO: 26) |

In some embodiments, the VEGF-A-binding proteins comprise a light chain domain having an amino acid sequence of SEQ ID NO:8 modified to include at least two amino acid substitutions, one of which is selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$; and/or a heavy chain domain of SEQ ID NO:9 modified to include at least two amino acid substitutions, one of which is selected from a positive polar amino acid at $V_5$, and a neutral polar amino acid at $L_{180}$ or a positive polar amino acid at $L_{180}$; and/or an Fc domain of SEQ ID NO:10 modified to include at least two amino acid substitutions, one of which is selected from a positive polar amino acid at position $L_{17}$, a positive polar amino acid at position $I_{35}$, a positive polar amino acid at position $V_{64}$, and a positive polar amino acid at position $L_{91}$.

In some embodiments, the VEGF-A-binding proteins comprise a light chain domain having an amino acid sequence of SEQ ID NO:8 modified to include at least one, at least two, at least three or at least four amino acid substitutions, one of which is selected from a negative polar amino acid at $F_{50}$, a positive polar amino acid at $V_{110}$, a negative polar amino acid at $L_{154}$ or a positive polar amino acid at $L_{154}$, and a positive polar amino acid at $L_{201}$; and/or a heavy chain domain of SEQ ID NO:9 modified to include at least two amino acid substitutions, one of which is a positive polar amino acid at $V_5$, and one of which is a neutral polar amino acid at $L_{180}$ or a positive polar amino acid at $L_{180}$; and/or an Fc domain of SEQ ID NO:10 modified to include at least one, at least two, at least three or at least four amino acid substitutions, one of which is a positive polar amino acid at position $L_{17}$, one of which is a positive polar amino acid at position $I_{35}$, one of which is a positive polar amino acid at position $V_{64}$, and one of which is a positive polar amino acid at position $L_{91}$.

In some embodiments, the negative polar amino acid at $F_{50}$ and/or $L_{154}$ of SEQ ID NO:8 is aspartic acid (D) or glutamic acid (E). In some embodiments, the neutral polar amino acid at $L_{180}$ of SEQ ID NO:9 is selected asparagine (N), cysteine (C), glutamine (Q), histidine (H), serine (S), threonine (T) or tyrosine (Y). In some embodiments, the positive polar amino acid at $V_{110}$, $L_{154}$ and/or $L_{201}$ of SEQ ID NO:8, at $V_5$ and/or $L_{180}$ of SEQ ID NO:9, and/or at $L_{17}$, $I_{35}$, $V_{64}$ and/or $L_{91}$ of SEQ ID NO:10 is arginine (R) or lysine (K).

In some embodiments, the VEGF-A-binding proteins comprise a light chain domain having an amino acid sequence of SEQ ID NO:8, a heavy chain domain having an amino acid sequence of SEQ ID NO:9, a human IgG Fc domain, or an Fc domain having an amino acid sequence of SEQ ID NO:10.

In some embodiments, the VEGF-A-binding proteins comprise a light chain domain having an amino acid sequence of SEQ ID NO:13, SEQ ID NO:41, SEQ ID NO:42 or SEQ ID NO:43, where position 154 of SEQ ID NO:13 or position 50 of SEQ ID NO:41 is optionally modified to a negative polar amino acid, or where position 110 of SEQ ID NO:42 or position 201 of SEQ ID NO:43 is optionally modified to a positive polar amino acid. In some embodiments, the VEGF-A-binding proteins comprise a heavy chain domain having an amino acid sequence of SEQ ID NO:14 or SEQ ID NO:44, where position 180 of SEQ ID NO:14 is optionally modified to a neutral polar amino acid, or where position 5 of SEQ ID NO:44 is optionally modified to a positive polar amino acid. In some embodiments, the VEGF-A-binding proteins comprise an Fc domain having an amino acid sequence of SEQ ID NO:27, SEQ ID NO:28, SEQ ID NO:29, or SEQ ID NO:30, wherein position 17 of SEQ ID NO:27, position 35 of SEQ ID NO:28, position 64 of SEQ ID NO:29 or position 91 of SEQ ID NO:30 is optionally modified to a positive polar amino acid.

In some aspects of the invention, provided herein are VEGF-A-binding proteins comprising a light chain domain having an amino acid sequence of SEQ ID NO:8 modified to include at least one amino acid substitution selected from $F_{50}D$, $V_{110}K$, $L_{154}K$, $L_{154}D$ and $L_{201}K$, and/or a heavy chain domain having an amino acid sequence of SEQ ID NO:9 modified to include at least one amino acid substitution selected from $V_5K$, $L_{180}S$ and $L_{180}K$, and/or an Fc domain having an amino acid sequence of SEQ ID NO:10 modified to include at least one amino acid substitution selected from $L_{17}K$, $I_{35}K$, $V_{64}K$ and $L_{91}K$.

In some embodiments, the VEGF-A-binding proteins comprise a light chain domain having an amino acid sequence of SEQ ID NO:11, SEQ ID NO:45, SEQ ID NO:46, SEQ ID NO:47 or SEQ ID NO:48. In some embodiments, the VEGF-A-binding proteins comprise a heavy chain domain having an amino acid sequence of SEQ ID NO:12, SEQ ID NO:49 or SEQ ID NO:50. In some embodiments, the VEGF-A-binding proteins comprise an Fc domain having an amino acid sequence of SEQ ID NO:23, SEQ ID NO:24, SEQ ID NO:25 or SEQ ID NO:26.

In some embodiments, the VEGF-A-binding proteins comprise a light chain domain having an amino acid sequence of SEQ ID NO:8 modified to include at least one amino acid substitution selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$, and a heavy chain domain having an amino acid sequence of SEQ ID NO:9. In some embodiments, the negative polar amino acid at $F_{50}$ and/or $L_{154}$ of SEQ ID NO:8 may be D or E. In some embodiments, the positive polar amino acid at $V_{110}$, $L_{154}$ and/or $L_{201}$ of SEQ ID NO: 8 may be R or K.

In some embodiments, the VEGF-A-binding proteins comprise a light chain domain having an amino acid sequence of SEQ ID NO:8, and a heavy chain domain having an amino acid sequence of SEQ ID NO:9 modified to include at least one amino acid substitution selected from a positive polar amino acid at $V_5$, a neutral polar amino acid at $L_{180}$, and a positive polar amino acid at $L_{180}$. In some embodiments, the neutral polar amino acid at $L_{180}$ of SEQ ID NO:9 may be selected from N, C, Q, H, S, T and Y. In some embodiments, the positive polar amino acid at $V_5$ and/or $L_{180}$ of SEQ ID NO:9 may be R or K.

In some embodiments, the VEGF-A-binding proteins further comprise a human IgG1 Fc domain. In some embodiments, the VEGF-A-binding proteins further comprise an Fc domain having an amino acid sequence of SEQ ID NO:10. In some embodiments, the Fc domain having the amino acid sequence of SEQ ID NO:10 is modified to include at least one amino acid substitution selected from $L_{17}K$, $I_{35}K$, $V_{64}K$ and $L_{91}K$.

In some aspects of the invention, provided herein are VEGF-A-binding proteins comprising an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$. In some embodiments, the positive polar amino acid is arginine (R) or lysine (K). In some embodiments, the VEGF-A-binding proteins comprise an Fc domain having an amino acid sequence of SEQ ID NO:10 modified to include at least one amino acid substitution selected from $L_{17}K$, $I_{35}K$, $V_{64}K$ and $L_{91}K$.

In some embodiments, the VEGF-A-binding proteins comprise an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$; a light chain domain having an amino acid sequence of SEQ ID NO:8; and a heavy chain domain having an amino acid sequence of SEQ ID NO:9.

In some embodiments, the VEGF-A-binding proteins comprise an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$; a light chain domain having an amino acid sequence of SEQ ID NO:8 modified to include at least one amino acid substitution selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$; and a heavy chain domain having an amino acid sequence of SEQ ID NO:9.

In some embodiments, the VEGF-A-binding proteins comprise an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$; a light chain domain having an amino acid sequence of SEQ ID NO:8; and heavy chain domain having an amino acid sequence of SEQ ID NO:9 modified to include at least one amino acid substitution selected from a positive polar amino acid at $V_5$, a neutral polar amino acid at $L_{180}$, and a positive polar amino acid at $L_{180}$.

In some embodiments, the VEGF-A-binding proteins are in the form of monoclonal antibodies such as, for example, chimeric monoclonal antibodies or humanized monoclonal antibodies. In some embodiments, the VEGF-A-binding proteins are in the form of antigen-binding antibody fragments such as, for example, Fab antibody fragments. In some embodiments, the VEGF-A-binding proteins are in the form of antibody-like proteins such as, for example, fusion proteins, single-chain Fv antibody fragments, and/or minibodies. In some embodiments, the VEGF-A-binding proteins are conjugated to a toxin and/or a radioisotope.

In some embodiments, the VEGF-A-binding proteins are lyophilized. In some embodiments, the VEGF-A-binding proteins are in solution.

In some aspects of the invention, provided herein are compositions comprising any of the VEGF-A-binding proteins of the invention. In some embodiments, the compositions comprise VEGF-A-binding proteins comprising a light chain domain having an amino acid sequence of SEQ ID NO:8 modified to include at least one amino acid substitution selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$; and/or a heavy chain domain having an amino acid sequence of SEQ ID NO:9 modified to include at least one amino acid substitution selected from a positive polar amino acid at $V_5$, a neutral polar amino acid at $L_{180}$, and a positive polar amino acid at $L_{180}$, and/or an Fc domain having an amino acid sequence of SEQ ID NO:10 modified to include at least one amino acid substitution selected from: a positive polar amino acid at position $L_{17}$, a positive polar amino acid at position $I_{35}$, a positive polar amino acid at position $V_{64}$, and a positive polar amino acid at position $L_{91}$. In some embodiments, the compositions comprise VEGF-A-binding proteins comprising a light chain domain having an amino acid sequence of SEQ ID NO:8 modified to include at least one amino acid substitution selected from $F_{50}D$, $V_{110}K$, $L_{154}K$, $L_{154}D$ and $L_{201}K$; and/or a heavy chain domain having an amino acid sequence of SEQ ID NO:9 modified to include at least one amino acid substitution selected from $V_5K$, $L_{180}S$ and $L_{180}K$. In some embodiments, the compositions comprise VEGF-A-binding proteins comprising an Fc domain having an amino acid sequence of SEQ ID NO:10 modified to include at least one amino acid substitution selected from a positive polar amino acid at position $L_{17}$, a positive polar amino acid at position $I_{35}$, a positive polar amino acid at position $V_{64}$, and a positive polar amino acid at position $L_{91}$. In some embodiments, the compositions comprise VEGF-A-binding proteins comprising an Fc domain having an amino acid sequence of SEQ ID NO:10 modified to include at least one amino acid substitution selected from $L_{17}K$, $I_{35}K$, $V_{64}K$ and $L_{91}K$.

In some embodiments, the compositions comprise the VEGF-A-binding proteins at a concentration of about 20 mg/ml to about 350 mg/ml. In some embodiments, the concentration of the VEGF-A-binding proteins is about 100 mg/ml to about 250 mg/ml. In some embodiments, the concentration of the VEGF-A-binding proteins is about 120 mg/ml to about 150 mg/ml. In some embodiments, the concentration of the VEGF-A-binding proteins is about 120 mg/ml, about 130 mg/ml or about 140 mg/ml. In some embodiments, the concentration of the VEGF-A-binding proteins is about 120 mg/ml or is 120 mg/ml.

In some embodiments, the compositions are liquid. In some embodiments, the compositions are formulated for subcutaneous injection and/or other non-intravenous delivery routes such as, for example, intramuscular injection.

In some embodiments, the compositions further comprise at least one buffer, at least one stabilizer and/or at least one surfactant. In some embodiments, the buffer is present at a concentration of about 1 mM to about 100 mM. In some embodiments, the buffer provides a pH of 5.5±2.0. In some embodiments, the stabilizer is present at a concentration of about 100 mM to about 500 mM. In some embodiments, a secondary stabilizer is present. In some embodiments, the secondary stabilizer is arginine, ornithine, lysine, histidine, glutamic acid, aspartic acid, isoleucine, leucine, alanine, phenylalanine, tyrosine, tryptophan, methionine, serine or proline (e.g., as a hydrochloride). In some embodiments, methionine is present at a concentration of about 5 mM to about 25 mM. In some embodiments, the surfactant is a nonionic surfactant. In some embodiments, the surfactant is present at a concentration of about 0.01% to about 0.1%. In some embodiments, the compositions further comprise at least one pharmaceutically acceptable carrier, excipient, and/or diluent. In some embodiments, the compositions further comprise additional agents (e.g., therapeutic agents). In some embodiments, the compositions are sterile.

In some embodiments, the compositions comprise the VEGF-A-binding proteins, histidine HCl, trehalose dehydrate, methionine and/or polysorbate 80. In some embodiments, the compositions comprise about 100 mg/ml to about 150 mg/ml of the VEGF-A-binding proteins, about 10 mM to about 30 mM histidine HCl, about 200 mM to about 220 mM trehalose dehydrate, about 5 mM to about 15 mM methionine and/or about 0.04% to about 0.08% polysorbate 80. In some embodiments, the compositions comprise about 120 mg/ml of the VEGF-A-binding proteins, about 20 mM histidine HCl, about 210 mM trehalose dehydrate, about 10 mM methionine and/or about 0.06% polysorbate 80.

In some aspects of the invention, provided herein are methods of treating a condition in a subject in need thereof, comprising administering to the subject any of the VEGF-A-binding proteins and/or compositions described herein. In some embodiments, the methods comprise administering to the subject a therapeutically effective amount of any of the VEGF-A-binding proteins and/or compositions provided herein. In some embodiments, the condition is cancer or a non-malignant condition. In some embodiments, the condition involves VEGF-A-expressing cells. In some embodiments, the cancer is a human cancer such as, for example, colorectal cancer, lung cancer, breast cancer, glioblastoma, kidney cancer, ovarian cancer, and other cancers expressing, or overexpressing VEGF-A.

In some aspects of the invention, provided herein are uses of the VEGF-A-binding proteins for the preparation of a medicament for treating a condition amenable to treatment with a VEGF-A-binding protein.

In some aspects of the invention, provided herein are nucleic acids encoding the VEGF-A-binding proteins, vectors comprising the nucleic acids, expression cassettes comprising the nucleic acids, and host cells comprising the nucleic acids and/or vectors and/or expression cassettes. In some embodiments, the nucleic acids are isolated.

In some aspects of the invention, provided herein are methods of producing a VEGF-A-binding protein (e.g., an anti-VEGF-A antibody), the methods comprising culturing any of the host cells described herein to produce the VEGF-A-binding protein. In certain embodiments, the methods include an additional step of isolating the VEGF-A-binding protein.

In some aspects of the invention, provided herein are kits comprising a container and any of the VEGF-A-binding proteins and/or compositions contained therein. In some embodiments, the kits further comprise instructions for using the kits. In some embodiments, the kits further comprise a package insert or label indicating that the kits can be used to treat cancer or a non-malignant condition such as, for example, one characterized by the overexpression of VEGF-A.

In some embodiments, the kits comprise injection components such as, for example, a syringe or a syringe filled with the VEGF-A-binding proteins or a composition containing the VEGF-A-binding proteins. In some embodiments, the volume of the composition in the kits is about 2 ml. In some embodiments, the volume of the composition is less than 2 ml. In some embodiments, the concentration of the VEGF-A-binding proteins in about 2 ml or less of a composition is about 100 mg/ml to about 150 mg/ml. In some embodiments, the concentration of the VEGF-A-binding proteins is about 120 mg/ml or is 120 mg/ml.

These and other aspects and embodiments of the invention will be described in greater detail herein.

BRIEF DESCRIPTION OF SEQUENCE LISTING

Figure 1:
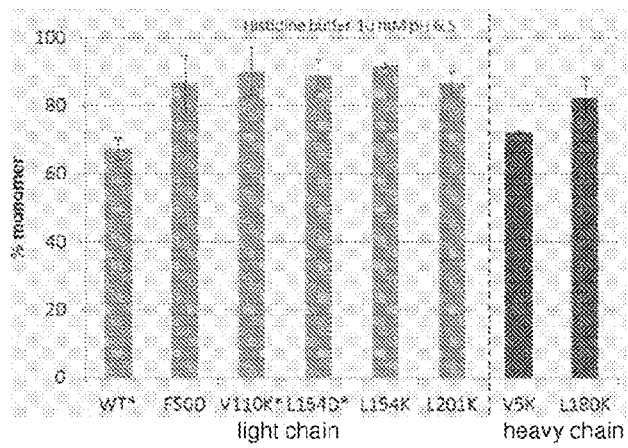
FIG. 1 is a graph showing percent monomer composition loss for select VEGF-A-binding proteins of the invention. Aggregation conditions were 50 mg/ml protein, 10 mM histidine HCl, pH 6.5, 52° C.

SEQ ID NO:1 is the amino acid sequence of a light chain domain of trastuzumab.

SEQ ID NO:2 is the amino acid sequence of an Fab heavy chain domain of trastuzumab.

SEQ ID NO:3 is the amino acid sequence of an Fc domain of trastuzumab.

SEQ ID NO:4 is the amino acid sequence of a light chain domain of trastuzumab modified at position $L_{154}D$.

SEQ ID NO:5 is the amino acid sequence of an Fab heavy chain domain of trastuzumab modified at position $L_{177}S$.

SEQ ID NO:6 is the amino acid sequence of a light chain domain of trastuzumab modified at position $L_{154}$.

SEQ ID NO:7 is the amino acid sequence of an Fab heavy chain domain of trastuzumab modified at position $L_{177}$.

SEQ ID NO:8 is the amino acid sequence of a light chain domain of bevacizumab.

SEQ ID NO:9 is the amino acid sequence of an Fab heavy chain domain of bevacizumab.

SEQ ID NO:10 is the amino acid sequence of an Fc domain of bevacizumab.

SEQ ID NO:11 is the amino acid sequence of a light chain domain of bevacizumab modified at position $L_{154}D$.

SEQ ID NO:12 is the amino acid sequence of an Fab heavy chain domain of bevacizumab modified at position $L_{180}S$.

SEQ ID NO:13 is the amino acid sequence of a light chain domain of bevacizumab modified at position $L_{154}$.

SEQ ID NO:14 is the amino acid sequence of an Fab heavy chain domain of bevacizumab modified at position $L_{180}$.

SEQ ID NO:15 is the amino acid sequence of an Fc domain of trastuzumab modified at position $L_{19}K$.

SEQ ID NO:16 is the amino acid sequence of an Fc domain of trastuzumab modified at position $I_{37}K$.

SEQ ID NO:17 is the amino acid sequence of an Fc domain of trastuzumab modified at position $V_{66}K$.

SEQ ID NO:18 is the amino acid sequence of an Fc domain of trastuzumab modified at position $L_{93}K$.

SEQ ID NO:19 is the amino acid sequence of an Fc domain of trastuzumab modified at position $L_{19}$.

SEQ ID NO:20 is the amino acid sequence of an Fc domain of trastuzumab modified at position $I_{37}$.

SEQ ID NO:21 is the amino acid sequence of an Fc domain of trastuzumab modified at position $V_{66}$.

SEQ ID NO:22 is the amino acid sequence of an Fc domain of trastuzumab modified at position $L_{93}$.

SEQ ID NO:23 is the amino acid sequence of an Fc domain of bevacizumab modified at position $L_{17}K$.

SEQ ID NO:24 is the amino acid sequence of an Fc domain of bevacizumab modified at position $I_{35}K$.

SEQ ID NO:25 is the amino acid sequence of an Fc domain of bevacizumab modified at position $V_{64}K$.

SEQ ID NO:26 is the amino acid sequence of an Fc domain of bevacizumab modified at position $L_{91}K$.

SEQ ID NO:27 is the amino acid sequence of an Fc domain of bevacizumab modified at position $L_{17}$.

SEQ ID NO:28 is the amino acid sequence of an Fc domain of bevacizumab modified at position $I_{35}$.

SEQ ID NO:29 is the amino acid sequence of an Fc domain of bevacizumab modified at position $V_{64}$.

SEQ ID NO:30 is the amino acid sequence of an Fc domain of bevacizumab modified at position $L_{91}$.

SEQ ID NO:31 is the amino acid sequence of Human Epidermal Growth Factor Receptor 2 (HER2; also referred to as receptor tyrosine-protein kinase erbB-2 precursor) (NCBI Reference Sequence NP_004439).

SEQ ID NO:32 is the amino acid sequence of Vascular Endothelial Growth Factor A (VEGF-A) (GenBank Protein ID AAA35789.1).

SEQ ID NO:33 is the human optimized nucleotide sequence of a light chain domain of trastuzumab, including the italicized restrictions sites used for subcloning into the GWIZ expression vector. The underlined sequence represents the leader sequence that includes the start codon and is removed during posttranslational modification.

SEQ ID NO:34 is the human optimized nucleotide sequence of a heavy chain domain (including Fc domain) of trastuzumab, including the italicized restrictions sites used for subcloning into the GWIZ expression vector. The underlined sequence represents the leader sequence that includes the start codon and is removed during posttranslational modification.

SEQ ID NO:35 is the nucleotide sequence of a light chain domain of bevacizumab, including the italicized restrictions sites used for subcloning into the GWIZ expression vector. The underlined sequence represents the leader sequence that includes the start codon and is removed during posttranslational modification.

SEQ ID NO:36 is the nucleotide sequence of a heavy chain domain (including Fc domain) of trastuzumab, including the italicized restrictions sites used for subcloning into the GWIZ expression vector. The underlined sequence represents the leader sequence that includes the start codon and is removed during posttranslational modification.

SEQ ID NO:37 is the amino acid sequence of an Fab heavy chain domain of trastuzumab modified at position $V_5$.

SEQ ID NO:38 is the amino acid sequence of a light chain domain of trastuzumab modified at position $L_{154}K$.

SEQ ID NO:39 is the amino acid sequence of an Fab heavy chain domain of trastuzumab modified at position $V_5K$.

SEQ ID NO:40 is the amino acid sequence of an Fab heavy chain domain of trastuzumab modified at position $L_{177}K$.

SEQ ID NO:41 is the amino acid sequence of a light chain domain of bevacizumab modified at position $F_{50}$.

SEQ ID NO:42 is the amino acid sequence of a light chain domain of bevacizumab modified at position $V_{110}$.

SEQ ID NO:43 is the amino acid sequence of a light chain domain of bevacizumab modified at position $L_{201}$.

SEQ ID NO:44 is the amino acid sequence of an Fab heavy chain domain of bevacizumab modified at position $V_5$.

SEQ ID NO:45 is the amino acid sequence of a light chain domain of bevacizumab modified at position $F_{50}D$.

SEQ ID NO:46 is the amino acid sequence of a light chain domain of bevacizumab modified at position $V_{110}K$.

SEQ ID NO:47 is the amino acid sequence of a light chain domain of bevacizumab modified at position $L_{154}K$.

SEQ ID NO:48 is the amino acid sequence of a light chain domain of bevacizumab modified at position $L_{201}K$.

SEQ ID NO:49 is the amino acid sequence of an Fab heavy chain domain of bevacizumab modified at position $V_5K$.

SEQ ID NO:50 is the amino acid sequence of an Fab heavy chain domain of bevacizumab modified at position $L_{180}K$.

SEQ ID NO:51 is the amino acid sequence of a light chain domain of trastuzumab modified at position $E_{195}N$.

SEQ ID NO:52 is the amino acid sequence of an Fab heavy chain domain of trastuzumab modified at position $L_{115}N$.

DETAILED DESCRIPTION OF INVENTION

Compositions containing proteins (e.g., monoclonal antibodies) are, in many instances, injected or infused via the intravenous route of administration. There is a desire to provide compositions for subcutaneous injection, which can be administered outside of the clinical setting and without a medical practitioner's assistance. Viscoelastic resistance to hydraulic conductance in the subcutaneous tissue, backpressure generated upon injection, and perceptions of pain all limit subcutaneous injection volumes to approximately 2 ml. Therefore, protein compositions for subcutaneous injection must contain highly concentrated, stable proteins. The preparation of highly concentrated protein compositions is challenging because, at high concentrations, many proteins begin to aggregate causing protein degradation and, in some cases, immunogenicity of the protein. Immunogenic reaction against aggregates of protein may lead to the production of neutralizing antibodies, which can render the protein ineffective over time.

The invention provides, inter alia, Human Epidermal Growth Factor Receptor 2 (HER2)-binding proteins and Vascular Endothelial Growth Factor-A (VEGF-A)-binding proteins that have a reduced tendency to aggregate (e.g., are more stable) as compared to existing proteins. The invention also provides compositions comprising the proteins and methods of use.

The exposure of hydrophobic residues to an aqueous solvent is a thermodynamically unfavorable condition and processes such as aggregation, which minimize exposure of these residues, are favored (Roberts, C. J. *J. Phys. Chem.*, 2003; 107(5): 1194-1207). This aggregation leads to protein degradation. The present invention is premised, in part, on the identification of HER2-binding proteins and VEGF-A-binding proteins having a reduced tendency to aggregate, for example, when present in compositions (e.g., liquid composition). Surprisingly, prior to the invention, the inventors found that they were not able to predict what amino acid modifications or what combinations of amino acid modifications reduce the tendency of HER2-binding proteins and VEGF-A-binding proteins to aggregate. A simple amino acid substitution in an existing protein from a hydrophobic residue to any hydrophilic residue did not necessarily reduce the tendency of the protein to aggregate. Rather, the inventors found that myriad factors affect protein aggregation, including the number of amino acid substitutions in the protein, the location of such substitutions, side-chain polarity, side-chain charge, and proximity of side chains relative to one another, and that only certain substitutions actually resulted in reduced aggregation.

Proteins

The invention provides, inter alia, HER2-binding proteins and VEGF-A-binding proteins that are less prone to aggregation as compared to existing proteins.

HER2-Binding Proteins

In some aspects of the invention, provided herein are proteins that selectively bind to cell antigen HER2 (i.e., HER2 antigen) and are referred to as "HER2-binding proteins." A protein (e.g., anti-HER2 antibody) selectively binds to an antigen (e.g., HER2) if the protein binds or is capable of binding to the antigen with a greater affinity than the affinity with which the protein might bind to other proteins (e.g., proteins other than HER2). Such binding may be measured or determined by standard protein-protein interaction assays (e.g., antibody-antigen or ligand-receptor assays) such as, for example, competitive assays, saturation assays, or standard immunoassays including, without limitation, enzyme-linked immunosorbant assays, radioimmunoassays and radio-immuno-filter binding assays.

HER2 protein has a molecular weight of approximately 138 kD. It is involved in transmembrane receptor protein tyrosine kinase activity. In some embodiments, the HER2 antigen may be human HER2 antigen. An example of an amino acid sequence of a human HER2 antigen is represented as NCBI Reference Sequence NP_004439.2 (SEQ ID NO:31).

In some embodiments, the HER2-binding proteins of the invention may comprise a light chain domain having an amino acid sequence of SEQ ID NO:1, or a light chain domain having an amino acid sequence of SEQ ID NO:1 modified to include at least one amino acid substitution at the leucine at position 154 ($L_{154}$). Leucine is a neutral nonpolar amino acid. In some embodiments, the invention contemplates substituting neutral nonpolar amino acids with negative polar amino acids. In some embodiments, $L_{154}$ may be substituted for a negative polar amino acid. Negative polar amino acids include aspartic acid (D) and glutamic acid (E). In some embodiments, the invention contemplates substituting neutral nonpolar amino acids with positive polar amino acids. In some embodiments, $L_{154}$ may be substituted for a positive polar amino acid. Positive polar amino acids include arginine (R) and lysine (K).

The amino acid substitution in the sequence of SEQ ID NO:1 may be $L_{154}D$ (leucine to aspartic acid at position 154) or $L_{154}K$ (leucine to lysine at position 154). In some embodiments, the HER2-binding proteins may have at least two amino acid substitutions in the sequence of SEQ ID NO:1, one of which is an amino acid substitution at $L_{154}$.

In some embodiments, the HER2-binding proteins may comprise a heavy chain domain having an amino acid sequence of SEQ ID NO:2, or a heavy chain domain having an amino acid sequence of SEQ ID NO:2 modified to include at least one amino acid substitution selected from the valine at position 5 ($V_5$) and the leucine at position 177 ($L_{177}$). In some embodiments, $V_5$ may be substituted with a positive polar amino acid. In some embodiments, the positive polar amino acid may be lysine. Thus, in some embodiments, the amino acid substitution may be $V_5K$. In some embodiments, $L_{177}$ may be substituted with a neutral polar amino acid. In some embodiments, the neutral polar amino acid may be serine. Thus, in some embodiments, the amino acid substitution may be $L_{177}S$. In some embodiments, $L_{177}$ may be substituted with a positive polar amino acid. In some embodiments, the positive polar amino acid may be lysine. Thus, in some embodiments, the amino acid substitution may be $L_{177}K$. In some embodiments, the HER2-binding protein may have at least two amino acid substitutions in the sequence of SEQ ID NO:2, one of which is an amino acid substitution at $V_5$. In some embodiments, the HER2-binding protein may have at least two amino acid substitutions in the sequence of SEQ ID NO:2, one of which is an amino acid substitution at $L_{177}$.

The amino acids, used according to the invention, may be naturally occurring or synthetic. Naturally occurring neutral polar amino acids include asparagine (N), cysteine (C), glutamine (Q), histidine (H), serine (S), threonine (T), and tyrosine (Y). Naturally occurring positively charged polar amino acids (i.e., positive polar amino acids) include arginine (R) and lysine (K). Naturally occurring negatively charged polar amino acids (i.e., negative polar amino acids) include aspartic acid (D) and glutamic acid (E).

In some embodiments, the HER2-binding proteins may comprise a human IgG Fc domain. In some embodiments, the HER2-binding proteins may comprise an Fc domain having an amino acid sequence of SEQ ID NO:3, or an Fc domain having an amino acid sequence of SEQ ID NO:3 modified to include at least one amino acid substitution at the leucine at position 19 ($L_{19}$), the isoleucine at position 37 ($I_{37}$), the valine at position 66 ($V_{66}$), and/or the leucine at position 93 ($L_{93}$). At least one amino acid substitution may be selected from $L_{19}K$, $I_{37}K$, $V_{66}K$ and $L_{93}K$.

In some embodiments, the HER2-binding proteins may comprise a modified light chain domain having the sequence of SEQ ID NO:4, SEQ ID NO:6, or SEQ ID NO:38 or a light chain domain having an amino acid sequence of SEQ ID NO:1; and/or a modified heavy chain domain having the sequence of SEQ ID NO:5, SEQ ID NO:7, SEQ ID NO:37, SEQ ID NO: 39 or SEQ ID NO:40 or a heavy chain domain having an amino acid sequence of SEQ ID NO:2; and/or a human IgG1 Fc domain, any of the modified Fc domains described herein (e.g., SEQ ID NOs. 15-22), or an Fc domain having an amino acid sequence of SEQ ID NO:3.

In certain embodiments, the neutral nonpolar amino acid at $L_{154}$ of SEQ ID NO:1, or at $L_{177}$ of SEQ ID NO:2, or at $L_{19}K$, $I_{37}K$, $V_{66}K$ and/or $L_{93}K$ of SEQ ID NO:3 may be substituted for a charged (e.g., positive or negative) or neutral polar amino acid. In some embodiments, the neutral nonpolar amino acid at $L_{154}$ of SEQ ID NO:1 is not lysine (K). In some embodiments, the neutral nonpolar amino acid at $L_{177}$ of SEQ ID NO:2 is not K.

In some embodiments, the HER2-binding proteins may comprise a light chain domain having an amino acid sequence of SEQ ID NO:1 modified to include an amino acid substitution of $E_{195}N$. In some embodiments, the HER2-binding proteins may comprise a heavy chain domain having an amino acid sequence of SEQ ID NO:2 modified to include an amino acid substitution of $L_{115}N$. In some embodiments, the HER2-binding proteins may comprise a light chain domain having an amino acid sequence of SEQ ID NO:1 modified to include an amino acid substitution of $E_{195}N$ and a heavy chain domain having an amino acid sequence of SEQ ID NO:2 modified to include an amino acid substitution of $L_{115}N$.

In some embodiments, the HER2-binding proteins may comprise a modified light chain domain having the sequence of SEQ ID NO:51. In some embodiments, the HER2-binding proteins may comprise a modified heavy chain domain having the sequence of SEQ ID NO:52. In some embodiments, the HER2-binding proteins may comprise a modified light chain domain having the sequence of SEQ ID NO:51 and a modified heavy chain domain having the sequence of SEQ ID NO:52.

VEGF-A-Binding Proteins

In some aspects of the invention, provided herein are proteins that may selectively bind to cell antigen VEGF-A (i.e., VEGF-A antigen) and are referred to as "VEGF-A-binding proteins." VEGF-A protein is a growth factor active in angiogenesis, vasculogenesis and endothelial cell growth. It induces endothelial cell proliferation, promotes cell migration, inhibits apoptosis, and induces permeabilization of blood vessels. VEGF-A binds to the VEGFR1/Flt-1 and to VEGFR2/Kdr receptors, heparan sulfate and heparin. In some embodiments, the VEGF-A antigen may be human VEGF-A antigen. An example of an amino acid sequence of a human VEGF-A antigen is represented as GenBank Protein ID AAA35789.1 (SEQ ID NO:32).

In some embodiments, the VEGF-A-binding proteins of the invention may comprise a light chain domain having an amino acid sequence of SEQ ID NO:8, or a light chain domain having an amino acid sequence of SEQ ID NO:8 modified to include at least one amino acid substitution selected from the phenylalanine at position 50 ($F_{50}$), the valine at position 110 ($V_{110}$), the leucine at position 154 ($L_{154}$), and the leucine at position 201 ($L_{201}$). Phenylalanine, valine and leucine are nonpolar amino acids. In some embodiments, the invention contemplates substituting a neutral nonpolar amino acid with a negative polar amino acid. In some embodiments, $F_{50}$ and/or $L_{154}$ may be substituted for a negative polar amino acid such asaspartic acid (D) or glutamic acid (E). In some embodiments, the invention contemplates substituting a neutral nonpolar amino acid with a positive polar amino acid. In some embodiments, $V_{150}$ and/or $L_{201}$ may be substituted for a positive polar amino acid such as arginine (R) or lysine (K).

The amino acid substitution in the sequence of SEQ ID NO:8 may be selected from $F_{50}D$ (phenylalanine to aspartic acid at position 50), $V_{110}K$ (valine to lysine at position 110), $L_{154}K$ (leucine to lysine at position 154), $L_{154}D$ (leucine to aspartic acid at position 154) and $L_{201}K$ (leucine to lysine at position 201). In some embodiments, the VEGF-A-binding proteins may have at least two amino acid substitutions in the sequence of SEQ ID NO:8, any of which may be an amino acid substitution selected from $F_{50}$, $V_{110}$, $L_{154}$, and $L_{201}$.

In some embodiments, the VEGF-A-binding proteins may comprise a heavy chain domain having an amino acid sequence of SEQ ID NO:9, or a heavy chain domain having an amino acid sequence of SEQ ID NO:9 modified to include at least one amino acid substitution selected from the valine at position 5 ($V_5$) and the leucine at position 180

($L_{180}$). In some embodiments, $V_5$ and/or $L_{180}$ may be substituted with a positive polar amino acid. In some embodiments, the positive polar amino acid may be lysine. Thus, in some embodiments, the amino acid substitution may be $V_5$K and/or $L_{180}$K. In some embodiments, $L_{180}$ may be substituted with a neutral polar amino acid. In some embodiments, the neutral polar amino acid may be serine. Thus, in some embodiments, the amino acid substitution may be $L_{180}$S. In some embodiments, the VEGF-A-binding proteins may have at least two amino acid substitutions in the sequence of SEQ ID NO:9, any of which may be an amino acid substitution selected from $V_5$ and $L_{180}$.

In some embodiments, the VEGF-A-binding proteins may comprise a human IgG Fc domain. In some embodiments, the VEGF-A-binding proteins may comprise an Fc domain having an amino acid sequence of SEQ ID NO:10, or an Fc domain having an amino acid sequence of SEQ ID NO:10 modified to include at least one amino acid substitution at the leucine at position 17 ($L_{17}$), the isoeucine at position 35 ($I_{35}$), the valine at position 64 ($V_{64}$), and/or the leucine at position 91 ($L_{91}$). At least one amino acid substitution may be selected from $L_{17}$K, $I_{35}$K, $V_{64}$K and $L_{91}$K.

In some embodiments, the VEGF-A-binding proteins may comprise a modified light chain domain having the sequence of SEQ ID NO:11, SEQ ID NO:13, SEQ ID NO:41, SEQ ID NO:45, SEQ ID NO:42, SEQ ID NO:46, SEQ ID NO:47, SEQ ID NO:43 or SEQ ID NO:48 or a light chain domain having an amino acid sequence of SEQ ID NO:8; and/or a modified heavy chain domain having the sequence of SEQ ID NO:12, SEQ ID NO:14, SEQ ID NO:44, SEQ ID NO:49 or SEQ ID NO:50 or a heavy chain domain having an amino acid sequence of SEQ ID NO:9; and/or a human IgG1 Fc domain, any of the modified Fc domains described herein (e.g., SEQ ID NOs. 23-30), or an Fc domain having an amino acid sequence of SEQ ID NO:10.

In certain embodiments, the neutral nonpolar amino acid at $F_{50}$, $V_{110}$, $L_{154}$ and/or $L_{201}$ of SEQ ID NO:8, or at $V_5$ and/or $L_{180}$ of SEQ ID NO:9, or at $L_{17}$, $I_{35}$, $V_{64}$ and/or $L_{91}$ of SEQ ID NO:10 may be substituted for a charged (e.g., positive or negative) or neutral polar amino acid. In some embodiments, the neutral nonpolar amino acid at $L_{154}$ of SEQ ID NO:8 is not lysine (K). In some embodiments, the neutral nonpolar amino acid at $L_{180}$ of SEQ ID NO:9 is not K.

Antibodies

In some aspects of the invention, the HER2-binding proteins and VEGF-A-binding proteins of the invention may be antibodies. In some embodiments, the proteins are monoclonal antibodies such as, for example, chimeric, human or humanized monoclonal antibodies. In some embodiments, the anti-HER2 antibodies and/or the anti-VEGF-A antibodies of the invention may be humanized monoclonal antibodies.

As used herein, the term "antibody" refers to a whole antibody. In some embodiments, the proteins provided herein may be antigen-binding fragments of an antibody, or single antibody chains. An antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three subdomains, $C_{H1}$, $C_{H2}$ and $C_{H3}$. Each light chain is comprised of a light chain variable region (abbreviated herein as $V_L$) and a light chain constant region. The light chain constant region is comprised of one subdomain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies and proteins provided herein may be described in terms of proteolytic fragments including without limitation Fv, Fab, Fab' and F(ab')$_2$ fragments. Such fragments may be prepared by standard methods (see, e.g., Coligan et al. *Current Protocols in Immunology*, John Wiley & Sons, 1991-1997, incorporated herein by reference). An antibody may comprise at least three proteolytic fragments (i.e., fragments produced by cleavage with papain): two Fab fragments, each containing a light chain domain and a heavy chain domain (designated herein as a "Fab heavy chain domain") and one Fc fragment containing two Fc domains. Each light chain domain contains a $V_L$ and a $C_L$ subdomain, each Fab heavy chain domain contains a $V_H$ and a $C_{H1}$ subdomain, and each Fc domain contains a $C_{H2}$ and $C_{H3}$ subdomain.

As used herein, the term "monoclonal antibody" may refer to an antibody obtained from a single clonal population of immunoglobulins that bind to the same epitope of an antigen. Monoclonal antibodies have the same Ig gene rearrangement and thus demonstrate identical binding specificity. Methods for preparing monoclonal antibodies, as described herein, are known in the art. Monoclonal antibodies can be prepared by a variety of methods. For example, monoclonal antibodies may be made by a hybridoma method (see, e.g., Kohler et al., *Nature*, 1975, 256: 495, incorporated herein by reference), or may be made by recombinant DNA methods (see, e.g., U.S. Pat. No. 4,816, 567, incorporated herein by reference). The monoclonal antibodies may also be isolated from phage antibody libraries. (See e.g., Clarkson et al., *Nature*, 1991, 352: 624-628 and Marks et al., *J. Mol. Biol.*, 1991, 222: 581-597, incorporated herein by reference).

Human monoclonal antibodies may be made by any of the methods known in the art, including those disclosed in U.S. Pat. No. 5,567,610, U.S. Pat. No. 5,565,354, U.S. Pat. No. 5,571,893, Kozber, *J. Immunol.*, 1984, 133: 3001, Brodeur, et al., Monoclonal Antibody Production Techniques and Applications, p. 51-63 (Marcel Dekker, Inc., new York, 1987), and Boerner et al., *J. Immunol.*, 1991, 147: 86-95. Human antibodies may be obtained by recovering antibody-producing lymphocytes from the blood or other tissues of humans producing antibody to an antigen of interest (e.g., HER2 or VEGF-A). These lymphocytes can be treated to produce cells that grow independently in the laboratory under appropriate culture conditions. The cell cultures can be screened for production of antibodies to the antigen of interest and then cloned. Clonal cultures can be used to produce human monoclonal antibodies to HER2 and/or VEGF-A, or the genetic elements encoding the variable portions of the heavy and light chain of the antibodies can be cloned and inserted into nucleic acid vectors for production of antibodies of different types. In addition to the conventional methods for preparing human monoclonal antibodies, such antibodies may also be prepared by immunizing transgenic animals that are capable of producing human antibodies (e.g., Jakobovits, et al., *PNAS USA*, 1993, 90: 2551, Jakobovits, et al., *Nature*, 1993, 362: 255-258, Bruggermann, et al., *Year in Immunol.*, 1993, 7:33 and U.S. Pat. No. 5,569,825).

As used herein, "humanized monoclonal antibody" may refer to monoclonal antibodies having at least human constant regions and an antigen-binding region, such as one, two or three CDRs, from a non-human species. Humanized antibodies specifically recognize antigens of interest, but will not evoke an immune response in humans against the antibody itself. As an example, murine CDRs may grafted into the framework region of a human antibody to prepare the humanized antibody (e.g., L. Riechmann, et al., *Nature*, 1988, 332, 323, and M. S. Neuberger et al., *Nature*, 1985, 314, 268). Alternatively, humanized monoclonal antibodies may be constructed by replacing the non-CDR regions of non-human antibodies with similar regions of human antibodies while retaining the epitopic specificity of the original antibodies. For example, non-human CDRs and optionally some of the framework regions may be covalently joined to human FR and/or Fc/pFc' regions to produce functional antibodies.

As used herein, the term "chimeric antibody" may refer to a monoclonal antibody comprising a variable region from one source (e.g., species) and at least a portion of a constant region derived from a different source. In some embodiments, chimeric antibodies are prepared by recombinant DNA techniques. In some embodiments, the chimeric antibodies comprise a murine variable region and a human constant region. Such chimeric antibodies may, in some embodiments, be the product of expressed immunoglobulin genes comprising DNA segments encoding murine immunoglobulin variable regions and DNA segments encoding human immunoglobulin constant regions. Methods for producing chimeric antibodies involve conventional recombinant DNA and gene transfection techniques (see, e.g., Morrison, S. L., et al., *Proc. Natl. Acad. Sci. USA*, 1984, 81: 6851-6855; U.S. Pat. No. 5,202,238; and U.S. Pat. No. 5,204,244).

Antigen-binding antibody fragments are also encompassed by the invention. Only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. An isolated F(ab')2 fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Further, Fab fragments consist of a covalently bound antibody light chain and a portion of the antibody heavy chain denoted Fd (heavy chain variable region, referred to herein as Fab heavy chain domain). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')2 and Fv are employed with either standard immunological meanings (Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)). Well-known functionally active antibody fragments include but are not limited to F(ab')2, Fab, Fv and Fd fragments of antibodies. These fragments, which lack the Fc fragment of intact antibody, clear more rapidly from the circulation, and may have less non-specific tissue binding than an intact antibody (Wahl et al., *J. Nucl. Med.* 24:316-325 (1983)). For example, single-chain antibodies may be constructed in accordance with the methods described in U.S. Pat. No. 4,946,778. Such single-chain antibodies include the variable regions of the light and heavy chains joined by a flexible linker moiety. Methods for obtaining a single domain antibody ("Fd") which comprises an isolated variable heavy chain single domain, also have been reported (see, e.g., Ward, et al., *Nature*, 1989, 341: 644-646, disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, (see, e.g., Moore et al., U.S. Pat. No. 4,462,334). Other references describing the use and generation of antibody fragments include, e.g., Fab fragments (Tijssen, Practice and Theory of Enzyme Immunoassays (Elsevieer, Amsterdam, 1985)), Fv fragments (Hochman, et al., *Biochemistry*, 1973, 12: 1130; Sharon, et al., *Biochemistry*, 1976, 15: 1591; Ehrilch, et al., U.S. Pat. No. 4,355,023) and portions of antibody molecules (Audilore-Hargreaves, U.S. Pat. No. 4,470,925). Thus, antibody fragments may be constructed from intact antibodies without destroying the specificity of the antibodies for the HER2 or VEGF-A epitope.

In some embodiments, the HER2-binding proteins and the VEGF-A-binding proteins of the invention may be recombinant forms of antibodies. In some embodiments, the proteins may be stabilized Fv fragments having single chain Fv forms (e.g., scFv) and comprising a peptide linker joining the variable heavy chain and variable light chain domains. In other embodiments, the proteins may be Fv fragments stabilized by inter-chain disulfide linkage (e.g., dsFv). In some embodiments, the proteins may contain additional cysteine residues engineered to facilitate the conjoining of the variable heavy chain and variable light chain domains. In further embodiments, the proteins may be minibodies or single variable domain antibodies ("dAbs"). Minibodies may be genetically engineered antigen-binding constructs having structures reminiscent of antibodies (e.g., having Fab and/or Fc regions with a reduced number of variable and/or constant domains). In other embodiments, the proteins may include dimerization domains (e.g. "leucine zippers") or other chemical modifications.

In some embodiments, the antibodies (e.g., anti-HER2 antibodies and/or anti-VEGF-A antibodies) may exhibit an affinity for their target that is similar to (or greater than) the affinity exhibited by existing antibodies that bind to the same target. As an example, anti-HER2 antibodies of the invention may recognize and bind to HER2 antigen on cells with an affinity at least comparable to that of trastuzumab. As another example, anti-VEGF-A antibodies of the invention may recognize and bind to VEGF-A on cells with an affinity at least comparable to that of bevacizumab.

Nucleic Acids

In some aspects, provided herein are nucleic acids that encode the HER2-binding proteins and the VEGF-A-binding proteins of the invention. As used herein, the term "nucleic acid" may refer to single-stranded and double-stranded nucleic acids and ribonucleic acids as well as deoxyribonucleic acids. In some embodiments, the nucleic acids are double-stranded DNA such as cDNA or single-stranded RNA such as mRNA. Nucleic acids may comprise naturally occurring and/or synthetic nucleotides and can be naturally or synthetically modified, for example by methylation, 5'- and/or 3'-capping. The sequence of the nucleic acids may have any nucleotide sequence suitable for encoding the proteins of the invention. The nucleic acids may be one consecutive nucleic acid molecule or they may be composed of several nucleic acid molecules, each coding for a different part of the protein of the invention. In some embodiments, the nucleic acid sequences may be at least partially adapted to a specific codon usage, for example, human codon usage, of the host cells or organisms in which the nucleic acids are to be expressed. The nucleic acids may be double-stranded or single-stranded DNA or RNA.

If the antibodies of the invention are single chain constructs, the nucleic acids encoding them may be single nucleic acid molecules containing a coding region which codes for the entire antibody. If the antibodies are composed of more than one amino acid chain, the nucleic acids may be, for example, single nucleic acid molecules containing several coding regions each coding for one of the amino acid chains of the antibodies. In some embodiments, the coding regions may be separated by regulatory elements such as IRES elements in order to generate separate amino acid chains. In some embodiments, the nucleic acids may be composed of several nucleic acid molecules wherein each nucleic acid molecule may comprise one or more coding regions, each coding for one of the amino acid chains of the antibodies. The nucleic acids may also comprise additional nucleic acid sequences or other modifications which, for example, may code for other proteins, may influence the transcription and/or translation of the coding region(s), may influence the stability or other physical or chemical properties of the nucleic acid, or may have no function at all.

Conjugates

In some aspects, HER2-binding proteins and the VEGF-A-binding proteins of the invention may be a conjugate. As used herein, the term "conjugate" may refer two or more compounds which are linked together so that at least some of the properties from each compound are retained in the conjugate. Linking may be achieved by a covalent or non-covalent bond. In some embodiments, the compounds of the conjugate are linked via a covalent bond. The different compounds of a conjugate may be directly bound to each other via one or more covalent bonds between atoms of the compounds. Alternatively, the compounds may be bound to each other via a linker molecule wherein the linker is covalently attached to atoms of the compounds. If the conjugate is composed of more than two compounds, then these compounds may be, for example, linked in a chain conformation, one compound attached to the next compound, or several compounds each may be attached to one central compound.

Conjugates may comprise additional agents that are useful in therapy, diagnosis, prognosis and/or monitoring of a condition such as, for example, cancer. Examples of additional agents include, without limitation, antibodies or fragments of antibodies, enzymes, interaction domains, stabilizing domains, signaling sequences, detectable labels, fluorescent dyes, toxins, catalytic antibodies, cytolytic components, immunomodulators, immunoeffectors, MHC class I or class II antigens, chelators for radioactive labeling, radioisotopes, liposomes, transmembrane domains, viruses, and cells. In some embodiments, the additional agents are radionuclides or a cytotoxic agents capable of killing cells (e.g., cancer cells), such as chemotherapeutic agents. Examples of other agents that may be used include alkylating agents such as cisplatin, anti-metabolites, plant alkaloids and terpenoids, vinca alkaloids, podophyllotoxin, taxanes such as taxol, topoisomerase inhibitors such as irinotecan and topotecan, and/or antineoplastics such as doxorubicin.

Vectors and Expression Cassettes

In some aspects, provided herein are vectors and/or expression cassettes comprising the proteins of the invention. As used herein, the term "vector" may refer to any intermediary vehicle for a nucleic acid which enables the nucleic acid, for example, to be introduced into prokaryotic and/or eukaryotic cells and, in some instances, to be integrated into a genome. Vectors of this kind may be replicated and/or expressed in the cells. Vectors may comprise plasmids, phagemids, bacteriophages or viral genomes. The term "plasmid," as used herein, may refer to a construct of extrachromosomal genetic material, for example, a circular DNA duplex, which can replicate independently of chromosomal DNA.

As used herein, the term "expression cassette" may refer to nucleic acid constructs which are capable of enabling and regulating the expression of coding nucleic acid sequences introduced therein. Expression cassettes may comprise promoters, ribosome binding sites, enhancers and/or other control elements which regulate transcription of a gene or translation of an mRNA. The exact structure of expression cassettes may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences may comprise a promoter region, which includes a promoter sequence for transcriptional control of operatively connected nucleic acids. Expression cassettes may also comprise enhancer sequences or upstream activator sequences.

As used herein, the term "promoter" refers to nucleic acid sequences which are located upstream (5') of the nucleic acid sequences which are to be expressed and control expression of the sequence by providing a recognition and binding site for RNA-polymerases. Promoters may include further recognition and binding sites for additional factors which may be involved in the regulation of gene transcription. Promoters may control the transcription of a prokaryotic or eukaryotic gene. Furthermore, promoters may be inducible, i.e., initiate transcription in response to an inducing agent, or may be constitutive if transcription is not controlled by an inducing agent. Genes which are under the control of inducible promoters are not expressed or are only expressed to a small extent if inducing agents are absent. In the presence of inducing agents the genes are switched on or the level of transcription is increased. This is mediated, in general, by binding of a specific transcription factor.

In addition, the expression cassettes or vectors may comprise other elements, for example, elements which may influence and/or regulate transcription and/or translation of the nucleic acids, amplification and/or reproduction of the expression cassettes or vectors, integration of the expression cassettes or vectors into the genome of host cells, and/or copy number of the expression cassettes or vectors in host cells. Suitable expression cassettes and vectors comprising respective expression cassettes for expressing proteins (e.g., antibodies) are well known.

Host Cells

In some embodiments, the HER2-binding proteins and VEGF-A binding proteins of the invention are produced by the host cells or cell lines as described above.

In some aspects, the invention provides host cells comprising the nucleic acids provided herein or the expression cassettes or vectors provided herein. The nucleic acids may be present in the form of a single copy or of two or more copies and, in some embodiments, are expressed in the host cells. As used herein, the term "host cell" may refer to any cell which can be transformed or transfected with an exogenous nucleic acid. They may be isolated cells or cells comprised in a tissue. The cells may be derived from a multiplicity of tissue types and may comprise primary cells and cell lines. Host cells may be prokaryotic (e.g., *E. coli*) or eukaryotic (e.g., mammalian, in particular human, yeast and/or insect).

In some embodiments, host cells are bacterial cells such as *E. coli*, yeast cells such as a *Saccharomyces* cells (e.g., *S. cerevisiae*), insect cells such as a Sf9 cells, or mammalian cells such as human cells, for example, tumor-derived human cells, hamster cells (e.g., Chinese Hamster Ovary cells), or primate cells. In some embodiments, the host cells are derived from human myeloid leukemia cells. Examples of cell lines for use herein include, without limitation, K562, KG1, MUTZ-3, NM-F9, NM-D4, NM-H9D8, NM-H9D8-E6, NM H9D8-E6Q12, GT-2X, and cells or cell lines derived from any of these host cells, or mixture of cells or cell lines comprising at least one of those cells. These cell lines and their properties are described in detail in the PCT application WO 2008/028686 A2.

In some embodiments, the host cells are optimized for expression of glycoproteins, in particular antibodies, having a specific glycosylation pattern. In some embodiments, the codon usage in the coding region of the nucleic acids and/or the promoters and the additional elements of the expression cassettes or vectors are compatible with and, in some instances, optimized for the type of host cell used.

Compositions

The invention also provides compositions comprising any of the HER2-binding proteins or VEGF-A-binding proteins, the nucleic acids, the expression cassettes and/or vectors, the host cells, or the conjugates, as described herein. The compositions may also contain more than one of these components. Furthermore, the compositions may comprise one or more additional components selected from buffers, solubilizers, surfactants, carriers, excipients, solvents, and/or diluents.

In some aspects of the invention, the compositions may comprise HER2-binding proteins comprising a light chain domain having an amino acid sequence of SEQ ID NO:1, or a light chain domain having an amino acid sequence of SEQ ID NO:1 modified to include at least one amino acid substitution of a negative polar amino acid at $L_{154}$ or a positive polar amino acid at $L_{154}$; and/or a heavy chain domain having an amino acid sequence of SEQ ID NO:2, or a heavy chain domain having an amino acid sequence of SEQ ID NO:2 modified to include at least one amino acid substitution selected from a positive polar amino acid at $V_5$, a positive polar amino acid at $L_{177}$, and a neutral polar amino acid at $L_{177}$; and/or a human IgG Fc domain, an Fc domain having an amino acid sequence of SEQ ID NO:3, or an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$.

In some embodiments, the compositions may comprise HER2-binding proteins comprising a light chain domain having an amino acid sequence of SEQ ID NO:1 modified to include at least one amino acid substitution selected from $L_{154}D$ and $L_{154}K$; and/or a heavy chain domain having an amino acid sequence of SEQ ID NO:2 modified to include at least one amino acid substitution selected from $V_5K$, $L_{177}K$ and $L_{177}S$; and/or a human IgG Fc domain or an Fc domain having an amino acid sequence of SEQ ID NO:3 modified to include at least one amino acid substitution selected from $L_{19}K$, $I_{37}K$, $V_{66}K$ and $L_{93}K$.

In some embodiments, the compositions may comprise HER2-binding proteins comprising a light chain domain having an amino acid sequence of SEQ ID NO:1 modified to include an amino acid substitution of $E_{195}N$. In some embodiments, the compositions may comprise HER2-binding proteins comprising a heavy chain domain having an amino acid sequence of SEQ ID NO:2 modified to include an amino acid substitution of $L_{115}N$. In some embodiments, the compositions may comprise HER2-binding proteins comprising a light chain domain having an amino acid sequence of SEQ ID NO:1 modified to include an amino acid substitution of $E_{195}N$ and a heavy chain domain having an amino acid sequence of SEQ ID NO:2 modified to include an amino acid substitution of $L_{115}N$.

In some aspects of the invention, the compositions may comprise VEGF-A-binding proteins comprising a light chain domain having an amino acid sequence of SEQ ID NO:8, or a light chain domain having an amino acid sequence of SEQ ID NO:8 modified to include at least one amino acid substitution selected from a negative polar amino acid at F50, a positive polar amino acid at $V_{110}$, a positive polar amino acid at $L_{154}$, a negative polar amino acid at $L_{154}$, and a positive polar amino acid at $L_{201}$; and/or a heavy chain domain having an amino acid sequence of SEQ ID NO:9, or a heavy chain domain having an amino acid sequence of SEQ ID NO:9 modified to include at least one amino acid substitution selected from a positive polar amino acid at $V_5$, a positive polar amino acid at $L_{180}$, and a neutral polar amino acid at $L_{180}$; and/or a human IgG Fc domain, an Fc domain having an amino acid sequence of SEQ ID NO:10, or an Fc domain having an amino acid sequence of SEQ ID NO:10 modified to include an amino acid substitution of a positive polar amino acid at position $L_{17}$, a positive polar amino acid at position $I_{35}$, a positive polar amino acid at position $V_{64}$, and a positive polar amino acid at position $L_{91}$.

In some embodiments, the compositions may comprise VEGF-A-binding proteins comprising a light chain domain having an amino acid sequence of SEQ ID NO:8 modified to include at least one amino acid substitution selected from $F_{50}D$, $V_{110}K$, $L_{154}K$, $L_{154}D$ and $L_{201}K$; and/or a heavy chain domain having an amino acid sequence of SEQ ID NO:9 modified to include at least one amino acid substitution selected from $V_5K$, $L_{180}K$ and $L_{180}S$; and/or a human IgG Fc domain or an Fc domain having an amino acid sequence of SEQ ID NO:10 modified to include at least one amino acid substitution selected from $L_{17}K$, $I_{35}K$, $V_{64}K$ and $L_{91}K$.

In some embodiments, the compositions may comprise the proteins provided herein at a concentration of about 20 mg/ml to about 350 mg/ml. In some embodiments, the protein concentration may be about 30 mg/ml to about 340 mg/ml, about 40 mg/ml to about 330 mg/ml, about 50 mg/ml to about 320 mg/ml, about 60 mg/ml to about 310 mg/ml, about 70 mg/ml to about 300 mg/ml, about 80 mg/ml to about 290 mg/ml, about 90 mg/ml to about 280 mg/ml, about 100 mg/ml to about 270 mg/ml, 110 mg/ml to about 260 mg/ml, 120 mg/ml to about 250 mg/ml, 130 mg/ml to about 240 mg/ml, 140 mg/ml to about 230 mg/ml, 150 mg/ml to about 220 mg/ml, 160 mg/ml to about 210 mg/ml, 170 mg/ml to about 200 mg/ml, or about 180 mg/ml to about 190 mg/ml. In some embodiments, the protein concentration is greater than 100 mg/ml. In some embodiments, the protein concentration is 120±20 mg/ml. In some embodiments, the protein concentration is about 50 mg/ml, about 75 mg/ml, about 100 mg/ml, about 110 mg/ml, about 120 mg/ml, about 130 mg/ml, about 140 mg/ml, or about 150 mg/ml. In some embodiments, the protein concentration is 110 mg/ml, 120 mg/ml, 130 mg/ml, 140 mg/ml, or 150 mg/ml.

In some embodiments, the concentration of the HER2-binding proteins in the compositions is greater than the concentration of trastazumab (HERCEPTIN®) formulated for intravenous routes of administration. In other embodiments, the concentration of the VEGF-A-binding proteins in the compositions is greater than the concentration of bevacizumab (AVASTIN®) formulated for intravenous routes of administration.

In some embodiments, the compositions provided herein may comprise additional components such as, for example, at least one buffer, at least one stabilizer and/or at least one surfactant.

Examples of buffers that may be used in the compositions provided herein include, without limitation, histidine buffer, acetic acid buffer, citric acid buffer, L-histidine/HCl buffer, and combinations thereof. The buffer(s) may be present at a concentration of about 1 mM to about 100 mM. In some embodiments, the buffer(s) may be present at a concentration of about 1 mM, about 10 mM, about 20 mM, about 30 mM, about 40 mM, about 50 mM, about 60 mM, about 70 mM, about 80 mM, about 90 mM, or about 100 mM.

The pH of the compositions of the invention may be adjusted to about 4.5 to about 7.0. In some embodiments, the pH is 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7. In some embodiments, the pH is about 5.5. In some embodiments, the pH is 5.5±2. In some embodiments, the pH of the composition is adjusted independently from the buffer used. This pH may be obtained by adjustment with an acid or a base, or by using adequate buffer (or mixtures of buffer), or both.

Examples of stabilizers that may be used, e.g., as a primary stabilizer, in the compositions provided herein include, without limitation, salt (e.g., NaCl), carbohydrate, saccharide, amino acid(s) (e.g., methionine), and sugar (e.g., α,α-trehalose dehydrate). Other examples of stabilizers that may be used, e.g, as a secondary stabilizer, in the compositions provided herein include, without limitation, arginine, ornithine, lysine, histidine, glutamic acid, aspartic acid, isoleucine, leucine, alanine, phenylalanine, tyrosine, tryptophan, methionine, serine or proline (e.g., as a hydrochloride). The stabilizer(s) may be present at a concentration of about 5 mM to about 500 mM, about 5 mM to about 25 mM, about 15 mM to about 250 mM, about 100 mM to about 500 mM, or about 150 mM to about 250 mM. In some embodiments, the stabilizer(s) may be present at a concentration of about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, about 200 mM, about 210 mM, about 220 mM, about 230 mM, about 240 mM, about 250 mM, about 260 mM, about 270 mM, about 280 mM, about 290 mM, about 300 mM, about 310 mM, about 320 mM, about 330 mM, about 340 mM, about 350 mM, about 360 mM, about 370 mM, about 380 mM, about 390 mM, about 400 mM, about 410 mM, about 420 mM, about 430 mM, about 440 mM, about 450 mM, about 460 mM, about 470 mM, about 480 mM, about 490 mM, or about 500 mM. In some embodiments, the composition may comprise methionine at a concentration of about 5 mM to about 25 mM, or about 5 mM to about 15 mM. In some embodiments, the methionine concentration is about 10 mM.

Examples of surfactants that may be used in the compositions provided herein include, without limitation, nonionic surfactant(s) such as, for example, polysorbate (e.g., polysorbate 20 and polysorbate 80) and polyethylene-polypropylene copolymer. The surfactant(s) may be present at a concentration of about 0.01% to about 0.1% (weight/volume, w/v), about 0.02% to about 0.08% (w/v), about 0.02% to 0.06% (w/v), or about 0.06% (w/v). In some embodiments, the surfactant(s) may be present at a concentration of about 0.02% (w/v), about 0.03% (w/v), about 0.04% (w/v), about 0.05% (w/v), about 0.06% (w/v), about 0.07% (w/v), about 0.08% (w/v), about 0.09% (w/v), or about 0.1% (w/v).

In some embodiments, the HER2-binding proteins or the VEGF-A-binding proteins of the compositions provided herein may be lyophilized or in aqueous solution.

In some embodiments, the compositions may or may not be sterile. A sterile composition may be one that is aseptic or free from all living microorganisms and their spores.

In some embodiments, the compositions provided herein may further comprise pharmaceutically acceptable carriers, excipients and/or stabilizers (see, e.g., Remington's Pharmaceutical Sciences 16th edition, Osol, A. Ed., 1980, incorporated herein by reference). As used herein, pharmaceutically acceptable carriers may include without limitation solvents, dispersion media, coatings, antibacterial and antifungal agents, and isotonic and absorption delaying agents. Pharmaceutically acceptable carriers, excipients and/or stabilizers are non-toxic to recipients (e.g., human subjects) at the dosages and concentrations used. In some embodiments, the carriers, excipients and/or stabilizers are suitable for intravenous, intramuscular, subcutaneous, parenteral, spinal or epidermal administration (e.g., by injection or infusion).

Examples of carriers, excipients and/or stabilizers include, without limitation buffers such as phosphate, citrate, and/or other organic acids; antioxidants such as ascorbic acid and/or methionine; preservatives such as octadecyldimethylbenzyl ammonium chloride, hexamethonium chloride, benzalkonium chloride, benzethonium chloride, phenol, butyl or benzyl alcohol, alkyl parabens such as methyl or propyl parabens, catechol, resorcinol, cyclohexanol, 3-pentanol, and/or m-cresol; low molecular weight (e.g., less than about 10 residues) polypeptides; proteins such as serum albumin, gelatin, and/or immunoglobulins; hydrophilic polymers such as olyvinylpyrrolidone; amino acids such as glycine, glutamine, asparagine, histidine, arginine, and/or lysine; monosaccharides, disaccharides, and/or other carbohydrates including glucose, mannose, and/or dextrins; chelating agents such as EDTA; sugars such as sucrose, mannitol, trehalose and/or sorbitol; salt-forming counter-ions such as sodium; metal complexes such as Zn-protein complexes; and/or non-ionic surfactants such as TWEEN®, PLURONIC® and/or polyethylene glycol (PEG).

In some embodiments, the compositions may further comprise adjuvants such as, for example, preservatives, wetting agents, emulsifying agents and/or dispersing agents. In some embodiments, the compositions are sterilized and/or may comprise antibacterial and antifungal agents, for example, paraben, chlorobutanol, and/or phenol sorbic acid. In some embodiments, the composition may also comprise isotonic agents, such as sugars and/or sodium chloride. In some embodiments, the composition may further comprise agents that delay absorption such as aluminum monostearate and/or gelatin.

In some embodiments, the compositions provided herein may further comprise at least one additional active agent including, without limitation, cytotoxic agents, chemotherapeutic agents, cytokines and/or immunosuppressive agents.

In some embodiments, a composition provided herein may be substantially free of any additive that reduces aggregation of the HER2-binding proteins or the VEGF-A-binding proteins provided herein.

In some embodiments, the compositions provided herein may comprise HER2-binding proteins or VEGF-A-binding proteins entrapped in microcapsules prepared, for example, by coacervation techniques (e.g., hydroxymethylcellulose or gelatin-microcapsules) or by interfacial polymerization (e.g., poly-(methylmethacylate) microcapsules). In some embodiments, the compositions provided herein may comprise HER2-binding proteins or VEGF-A-binding proteins entrapped in colloidal drug delivery systems such as, for example, liposomes, albumin microspheres, microemulsions, nano-particles and nanocapsules. In some embodiments, the compositions provided herein may comprise HER2-binding proteins or VEGF-A-binding proteins entrapped in macroemulsions. See, e.g., Remington's Pharmaceutical Sciences 16th edition, Osol, A. Ed. (1980).

In some embodiments, the compositions provided herein may be sustained-release compositions.

In various aspects of the invention, provided herein are highly concentrated, stable liquid compositions of HER2-binding proteins or VEGF-A-binding proteins having a reduced tendency to aggregate. As used herein, "highly concentrated" compositions may refer to compositions comprising the proteins provided herein at a concentration of greater than 100 mg/ml (e.g., about 110 mg/ml to about 150 mg/ml). As used herein, "stable" compositions may refer to compositions comprising the proteins provided herein that retain (or essentially retain) physical stability and/or chemical stability and/or biological activity upon storage for an intended period of time (e.g., intended shelf-life of the composition) at an intended temperature (e.g., 2-8° C.). In some embodiments, the compositions may be stable following freezing (to, e.g., −20° C.) and thawing of the compositions, for example, following one or more cycles of freezing and thawing. Various analytical techniques for measuring protein stability are available in the art (see, e.g., Peptide and Protein Drug Delivery, 247-301, Vincent Lee Ed., Marcel Dekker, Inc., New York, N.Y., Pubs., 1991; and Jones, A. Adv. Drug Delivery Rev., 1993, 10: 29-90, each of which are incorporated herein by reference). Stability may be measured at a select temperature for a select time period. Stability may be evaluated qualitatively and/or quantitatively in a variety of different ways including, without limitation, evaluation of aggregate formation (e.g., using size exclusion chromatography, measuring turbidity, and/or visual inspection); assessment of charge heterogeneity using cation exchange chromatography or capillary zone electrophoresis; SDS-PAGE analysis to compare reduced and intact antibody; and/or evaluating biological activity or antigen binding function of the protein. Instability may involve aggregation, deamidation (e.g. Asn deamidation), oxidation (e.g., Met oxidation), isomerization (e.g. Asp isomeriation), clipping/hydrolysis/fragmentation (e.g., hinge region fragmentation), succinimide formation, and/or unpaired cysteine(s).

In some embodiments, the compositions, for example, the highly concentrated compositions, are formulated for subcutaneous or intramuscular delivery. In some embodiments, the compositions provided herein are considered to be highly concentrated compositions formulated for subcutaneous delivery if the protein concentration in the compositions is greater than 100 mg/ml (e.g., about 110 mg/ml to about 150 mg/ml) and the volume of the compositions is about or less than 2 ml. In some embodiments, the volume of the compositions is about 1.5 ml.

Examples of highly concentrated compositions comprising the HER2-binding proteins or the VEGF-A-binding proteins provided herein include, without limitation, the following:

(a) 100 to 150 mg/ml protein, 1 to 50 mM of a histidine buffer (e.g., L-histidine/HCl) at a pH of about 5.5, 15 to 250 mM of a stabilizer (e.g., α,α-trehalose dihydrate) and, optionally, methionine as a second stabilizer at a concentration of 5 to 25 mM, and polysorbate 20 or polysorbate 80 at a concentration of 0.02 to 0.06% (w/v);

(b) 120±20 mg/ml protein, 10 to 30 mM or 20 mM of a histidine buffer (e.g., L-histidine/HCl) at a pH of about 5.5, 150 to 250 mM or 210 mM of a stabilizer (e.g., α,α-trehalose dihydrate) and, optionally, methionine as a second stabilizer at a concentration of 5 to 25 mM, 5 to 15 mM or 10 mM, and polysorbate 20 or polysorbate 80 at a concentration of 0.02 to 0.06% (w/v);

(c) 120 mg/ml protein, 10 to 30 mM or 20 mM of a histidine buffer (e.g., L-histidine/HCl) at a pH of about 5.5, 150 to 250 mM or 210 mM of a stabilizer (e.g., α,α-trehalose dihydrate) and, optionally, methionine as a second stabilizer at a concentration of 5 to 25 mM, 5 to 15 mM, or 10 mM, and polysorbate 20 or polysorbate 80 at a concentration of 0.02 to 0.06% (w/v); and (d) 120 mg/ml protein, 20 mM of L-histidine/HCl at a pH of about 5.5, 210 mM α,α-trehalose dihydrate and, optionally, 10 mM methionine as a second stabilizer, and polysorbate 20 or polysorbate 80 at a concentration of 0.02 to 0.06% (w/v).

Methods of Use

The invention also provides methods of using the HER2-binding and VEGF-A-binding proteins and composition, for example, in in vitro, in situ and in vivo applications.

Examples of in vitro and in situ applications in accordance with the invention include, without limitation, cell killing assays, as positive controls for apoptosis assays, for purification or immunoprecipitation of antigen from cells, and for diagnostic assays.

Examples of in vivo applications in accordance with the invention include, without limitation, methods of treatment. In some embodiments, the proteins and protein compositions of the invention may be used to treat one or more condition(s) such as, for example, cancers and/or non-malignant conditions in a subject in need thereof. Thus, in some embodiments, provided herein are methods of treating cancers and/or non-malignant conditions in a subject in need thereof. In some embodiments, the methods of treatment comprise administering to the subject in need thereof a therapeutically effective amount of the proteins and/or compositions of the invention. The term "therapeutically effective amount" is described below.

In some embodiments, the proteins provided herein are administered at dosages of about 0.0001 mg/kg to about 100 mg/kg of the recipient (e.g., subject) body weight. In some embodiments, the proteins are administered at dosages of about 0.01 mg/kg to about 5 mg/kg of the recipient body weight. In some embodiments, the proteins are administered at dosages of 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg·kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or 10 mg/ml recipient body weight. In some embodiments, the proteins are administered at dosages of about 0.3 mg/kg body weight, about 1 mg/kg recipient body weight, about 3 mg/kg recipient body weight, about 5 mg/kg recipient body weight, about 10 mg/kg recipient body weight, or within the range of 1-10 mg/kg recipient body weight.

In some embodiments, the proteins provided herein are administered once per week, once every two weeks, once every three weeks, once every four weeks, once a month, once every three months or once every three to six months.

Dosage and frequency may vary depending on the half-life of the protein in the recipient. For example, in general, human antibodies show the longest half-life, followed by humanized antibodies, chimeric antibodies, and nonhuman antibodies.

Actual dosage levels of the proteins provided herein may be varied so as to obtain an amount of the proteins which is effective to achieve the desired response (e.g., therapeutic response) for a particular subject, composition, and mode of administration, without being toxic to the subject. The selected dosage level may depend upon a variety of pharmacokinetic factors including, without limitation, the activity of the proteins, the route of administration, the time of administration, the rate of excretion of the proteins, the duration of administration, other drugs, compounds and/or materials used in combination with the proteins, the age, sex, weight, condition, general health and prior medical history of the subject.

In some embodiments, the proteins and protein compositions provided herein may be administered at therapeutically effective amounts. As used herein, "therapeutically effective amount" of the proteins and/or the protein compositions may result in a decrease in severity of the symptoms of a condition, an increase in frequency and duration of symptom-free periods, or a prevention of impairment or disability due to the condition. For example, for administration of the proteins or compositions of the invention to a subject having tumors, a "therapeutically effective amount" inhibits cell growth or tumor growth by at least about 20%, by at least about 40%, by at least about 60%, or by at least about 80% relative to untreated subjects. The ability of the proteins to inhibit tumor growth may be evaluated in an animal model system predictive of efficacy in human tumors. Alternatively, the proteins may be evaluated by examining the ability of the proteins to inhibit tumor growth in vitro. In some embodiments, a therapeutically effective amount of the HER2-binding proteins or the VEGF-A-binding proteins may decrease tumor size, or otherwise ameliorate symptoms in a subject. One of ordinary skill in the art would be able to determine such amounts based on such factors as the subject's size, the severity of the subject's symptoms, and the particular composition or route of administration selected.

In some embodiments, the proteins and/or the compositions provided herein may be administered via one or more routes of administration using one or more of a variety of methods known in the art. In some embodiments, the proteins and/or the protein compositions are administered via subcutaneous, intravenous, intramuscular, intradermal, intraperitoneal, spinal or other parenteral routes of administration, for example by injection or infusion. As used herein, the term "parenteral administration" may refer to modes of administration other than enteral and topical administration, usually by injection, and includes, without limitation, subcutaneous, intravenous, intramuscular, intraarterial, intrathecal, intracapsular, intraorbital, intracardiac, intradermal, intraperitoneal, transtracheal, subcuticular, intraarticular, subcapsular, subarachnoid, intraspinal, epidural and intrasternal injection, and infusion. In other embodiments, the proteins and/or the protein compositions may be administered via a nonparenteral route, such as a topical, epidermal or mucosal route of administration, for example, intranasally, orally, vaginally, rectally, sublingually or topically.

Uses for HER2-Binding Proteins

In some embodiments, the HER2-binding proteins and compositions may be used to treat cancers such as, for example, breast cancer and/or other cancers expressing HER2

Uses for VEGF-A-Binding Proteins

In some embodiments, the VEGF-A-binding proteins and compositions may be used to treat cancers such as, for example, colorectal cancer, lung cancer, breast cancer, glioblastoma, kidney cancer, ovarian cancer, and/or other cancers expressing or overexpressing VEGF-A.

Kits

Other aspects of the invention provide kits comprising the HER2-binding or VEGF-A-binding proteins and compositions described herein. In some embodiments, kits may comprise a single container (e.g., a syringe or vial) containing a protein or composition of the invention.

In some embodiment, the volume of the composition may be less than or equal to 2 ml. In such embodiments, the concentration of the protein is greater than 100 mg/ml, for example about 110 mg/ml, about 120 mg/ml, about 130 mg/ml, about 140 mg/ml, or about 150 mg/ml. The kits may comprise a container(s) and a label or package insert on or associated with the container. Suitable containers include without limitation bottles, vials, and syringes. The containers may be formed from a variety of materials such as glass or plastic. The containers may hold a composition which may be administered to a subject and may have a sterile access port (for example the container may be an intravenous solution bag or a vial having a stopper pierceable by a hypodermic injection needle).

The label or package insert may indicate that kits are used for administering the proteins or protein compositions to a subject. The label or package insert may further comprise instructions for administration. As used herein, a "package insert" may refer to instructions customarily included in commercial packages of products that contain information about the product and its use, for example, indications, dosage, administration, contraindications and/or warnings concerning the use of such products. In some embodiments, the package insert may indicate that the proteins and protein compositions are used for treating cancer or autoimmune conditions.

Additionally, the kits may further comprise other containers comprising additional components including, without limitation, pharmaceutically-acceptable buffers, bacteriostatic water for injection (BWFI), phosphate-buffered saline, Ringer's solution and/or dextrose solution. The kits may also comprise other materials including, without limitation, other buffers, diluents, filters, needles, and/or syringes.

In some embodiments, provided herein are kits that may be useful for various purposes, e.g., for cell killing assays, as a positive control for apoptosis assays, for purification or immunoprecipitation of antigen from cells. For isolation and purification of antigen, the kit may contain an antibody coupled to beads (e.g., sepharose beads). Kits may contain the antibodies for detection and quantitation of HER2 or VEGF-A in vitro, e.g., in an ELISA or a Western blot.

The invention is further described by the following numbered paragraphs:

1. A HER2-binding protein comprising:
a light chain domain having an amino acid sequence of SEQ ID NO:1 modified to include an amino acid substitution of a negative polar amino acid at $L_{154}$ or a positive polar amino acid at $L_{154}$; and/or
a heavy chain domain having an amino acid sequence of SEQ ID NO:2 modified to include at least one amino acid substitution selected from a positive polar amino acid at $V_5$, a neutral polar amino acid at $L_{177}$, and a positive polar amino acid at $L_{177}$; and/or
an Fc domain having an amino acid sequence of SEQ ID NO:3 modified to include at least one amino acid substitution selected from a positive polar amino acid at position $L_{19}$, a positive polar amino acid at position $I_{37}$, a positive polar amino acid at position $V_{66}$, and a positive polar amino acid at position $L_{93}$.

2. The HER2-binding protein of paragraph 1, wherein the protein comprises a light chain domain having an amino acid sequence of SEQ ID NO:1 modified to include at least two amino acid substitutions; and/or a heavy chain domain of SEQ ID NO:2 modified to include at least two amino acid substitutions; and/or an Fc domain of SEQ ID NO:3 modified to include at least two amino acid substitutions.

3. The HER2-binding protein of paragraph 1 or 2, wherein the negative polar amino acid at $L_{154}$ of SEQ ID NO:1 is aspartic acid (D) or glutamic acid (E).

4. The HER2-binding protein of any of paragraphs 1-3, wherein the neutral polar amino acid at $L_{177}$ of SEQ ID NO:2 is selected from asparagine (N), cysteine (C), glutamine (Q), histidine (H), serine (S), threonine (T) or tyrosine (Y).

5. The HER2-binding protein of any of paragraphs 1-4, wherein the positive polar amino acid at $L_{154}$ of SEQ ID NO:1, at $V_5$ and/or $L_{177}$ of SEQ ID NO:2, and/or at $L_{19}$, $I_{37}$, $V_{66}$ and/or $L_{93}$ of SEQ ID NO:3 is arginine (R) or lysine (K).

6. The HER2-binding protein of any of paragraphs 1-5, wherein the protein comprises a light chain domain having an amino acid sequence of SEQ ID NO:1, a heavy chain domain having an amino acid sequence of SEQ ID NO:2, a human IgG Fc domain, or an Fc domain having an amino acid sequence of SEQ ID NO:3.

7. The HER2-binding protein of paragraph 1, wherein the protein comprises a light chain domain having an amino acid sequence of SEQ ID NO:6.

8. The HER2-binding protein of paragraph 1, wherein the protein comprises a heavy chain domain having an amino acid sequence of SEQ ID NO:7 or SEQ ID NO:37.

9. The HER2-binding protein of paragraph 1, wherein the protein comprises an Fc domain having an amino acid sequence of SEQ ID NO:19, SEQ ID NO:20, SEQ ID NO:21, or SEQ ID NO:22.

10. A HER2-binding protein comprising:
a light chain domain having an amino acid sequence of SEQ ID NO:1 modified to include an amino acid substitution of $L_{154}$D or $L_{154}$K; and/or a heavy chain domain having an amino acid sequence of SEQ ID NO:2 modified to include at least one amino acid substitution selected from $V_5$K, $L_{177}$S and $L_{177}$K; and/or an Fc domain having an amino acid sequence of SEQ ID NO:3 modified to include at least one amino acid substitution selected from $L_{19}$K, $I_{37}$K, $V_{66}$K and $L_{93}$K.

11. The HER2-binding protein of paragraph 10, wherein the protein comprises a light chain domain having an amino acid sequence of SEQ ID NO:1 modified to include at least two amino acid substitutions; and/or a heavy chain domain having an amino acid sequence of SEQ ID NO:2 modified to include at least two amino acid substitutions; and/or an Fc domain having an amino acid sequence of SEQ ID NO:3 modified to include at least two amino acid substitutions.

12. The HER2-binding protein of paragraph 10 or 11, wherein the protein comprises a light chain domain having an amino acid sequence of SEQ ID NO:1, a heavy chain domain having an amino acid sequence of SEQ ID NO:2, a human IgG Fc domain, or an Fc domain having an amino acid sequence of SEQ ID NO:3.

13. The HER2-binding protein of paragraph 10, wherein the protein comprises a light chain domain having an amino acid sequence of SEQ ID NO:4, SEQ ID NO:38 or SEQ ID NO:51.

14. The HER2-binding protein of paragraph 10, wherein the protein comprises a heavy chain domain having an amino acid sequence of SEQ ID NO:5, SEQ ID NO:39, SEQ ID NO:40 or SEQ ID NO:52.

15. The HER2-binding protein of paragraph 10, comprising an Fc domain having an amino acid sequence of SEQ ID NO:15, SEQ ID NO:16, SEQ ID NO:17, or SEQ ID NO:18.

16. The HER2-binding protein of any of paragraphs 1-15, wherein the protein is in the form of a monoclonal antibody 17. The HER2-binding protein of paragraph 16, wherein the monoclonal antibody is a chimeric, human or humanized monoclonal antibody.

18. The HER2-binding protein of any of paragraphs 1-15, wherein the protein is in the form of a fusion protein.

19. The HER2-binding protein of any of paragraphs 1-15, wherein the protein is in the form of an Fab antibody fragment, single-chain Fv antibody fragment, or minibody.

20. The HER2-binding protein of any of paragraphs 1-17, wherein the protein is conjugated to a diagnostic agent or a therapeutic agent.

21. The HER2-binding protein of any of paragraphs 1-20, comprising a light chain domain having an amino acid sequence of SEQ ID NO:1 modified to include an amino acid substitution of $E_{195}$N.

22. The HER2-binding protein of any of paragraphs 1-21, comprising a heavy chain domain having an amino acid sequence of SEQ ID NO:2 modified to include an amino acid substitution of $L_{115}$N.

23. A HER2-binding protein comprising:
   a light chain domain having an amino acid sequence of SEQ ID NO:1 modified to include an amino acid substitution of $E_{195}N$; and/or
   a heavy chain domain having an amino acid sequence of SEQ ID NO:2 modified to include an amino acid substitution of $L_{115}N$.

24. A composition comprising the HER2-binding protein of any of paragraphs 1-23.

25. The composition of paragraph 24, wherein the protein is present at a concentration of about 50 mg/ml to about 250 mg/ml.

26. The composition of paragraph 25, wherein the protein is present at a concentration of about 100 mg/ml to about 200 mg/ml.

27. The composition of paragraph 26, wherein the protein is present at a concentration of about 110 mg/ml to about 150 mg/ml.

28. The composition of paragraph 27, wherein the protein is present at a concentration of about 120 mg/ml.

29. The composition of paragraph 27, wherein the protein is present at a concentration of about 130 mg/ml.

30. The composition of any of paragraphs 24-29, wherein the composition further comprises at least one buffer, at least one stabilizer, and/or at least one surfactant.

31. The composition of any of paragraphs 24-30, wherein the composition is liquid.

32. The composition of paragraph 31, wherein the composition is formulated for subcutaneous injection.

33. The composition of any of paragraphs 24-32, wherein the composition is sterile.

34. The composition of any of paragraphs 24-33, wherein the composition further comprises histidine HCl, trehalose dehydrate, methionine and/or polysorbate.

35. The composition of paragraph 24, wherein the composition comprises about 110 to about 130 mg/ml HER2-binding protein, about 10 mM to about 30 mM histidine HCl, about 200 mM to about 220 mM trehalose dehydrate, about 5 mM to about 15 mM methionine, and/or about 0.04% to about 0.08% polysorbate 80.

36. A method of treating a condition in a subject in need thereof, comprising administering to the subject a therapeutically effective amount of the composition of any of paragraphs 24-35.

37. The method of paragraph 36, wherein the condition is cancer.

38. The method of paragraph 37, wherein the cancer is breast cancer.

39. A nucleic acid encoding the HER2-binding protein of any of paragraphs 1-23.

40. A vector comprising the nucleic acid of paragraph 39.

41. An expression cassette comprising the nucleic acid of paragraph 39.

42. A host cell comprising the nucleic acid of paragraph 39, the vector of paragraph 40, or the expression cassette of paragraph 41.

43. A method of producing an antibody, comprising culturing the host cell of paragraph 42.

44. A kit comprising a container and the HER2-binding protein of any of paragraphs 1-23 or the composition of any of paragraphs 24-35 contained therein.

45. The kit of paragraph 44, wherein the container is glass or plastic.

46. The kit of paragraph 44 or 45, wherein the container is a vial or a syringe.

47. The kit of any of paragraphs 44-46, wherein the kit further comprises instructions for using the kit.

48. The kit of any of paragraphs 44-47, wherein the kit further comprises a package insert or label indicating that the protein or composition can be used to treat cancer characterized by the overexpression of HER2.

49. The kit of any of paragraphs 44-48, wherein the composition is provided at a volume of less than about 2 ml or is about 2 ml.

50. The kit of paragraph 49, wherein the composition is provided at a volume of about 1.5 ml.

51. A VEGF-A-binding protein comprising:
   a light chain domain having an amino acid sequence of SEQ ID NO:8 modified to include at least one amino acid substitution selected from a negative polar amino acid at $F_{50}$, a positive polar amino acid at $V_{110}$, a negative polar amino acid at $L_{154}$, a positive polar amino acid at $L_{154}$, and a positive polar amino acid at $L_{201}$; and/or
   a heavy chain domain having an amino acid sequence of SEQ ID NO:9 modified to include at least one amino acid substitution selected from a positive polar amino acid at $V_5$, a neutral polar amino acid at $L_{180}$, and a positive polar amino acid at $L_{180}$; and/or
   an Fc domain having an amino acid sequence of SEQ ID NO:10 modified to include at least one amino acid substitution selected from: a positive polar amino acid at position $L_{17}$, a positive polar amino acid at position $I_{35}$, a positive polar amino acid at position $V_{64}$, and a positive polar amino acid at position $L_{91}$.

52. The VEGF-A-binding protein of paragraph 51, wherein the protein comprises a light chain domain having an amino acid sequence of SEQ ID NO:8 modified to include at least two amino acid substitutions; and/or a heavy chain domain of SEQ ID NO:9 modified to include at least two amino acid substitutions; and/or an Fc domain of SEQ ID NO:10 modified to include at least two amino acid substitutions.

53. The VEGF-A-binding protein of paragraph 51 or 52, wherein the negative polar amino acid at $F_{50}$ and/or $L_{154}$ of SEQ ID NO:8 is aspartic acid (D) or glutamic acid (E).

54. The VEGF-A-binding protein of any of paragraphs 51-53, wherein the neutral polar amino acid at $L_{180}$ of SEQ ID NO:9 is selected from asparagine (N), cysteine (C), glutamine (Q), histidine (H), serine (S), threonine (T) or tyrosine (Y).

55. The VEGF-A-binding protein of any of paragraphs 51-54, wherein the positive polar amino acid at $V_{110}$, $L_{154}$ and/or $L_{201}$ of SEQ ID NO:8, at $V_5$ and/or $L_{180}$ of SEQ ID NO:9, and/or at $L_{17}$, $I_{35}$, $V_{64}$ and/or $L_{91}$ of SEQ ID NO:10 is arginine (R) or lysine (K).

56. The VEGF-A-binding protein of any of paragraphs 51-55, wherein the protein comprises a light chain domain having an amino acid sequence of SEQ ID NO:8, a heavy chain domain having an amino acid sequence of SEQ ID NO:9, a human IgG Fc domain, or an Fc domain having an amino acid sequence of SEQ ID NO:10.

57. The VEGF-A-binding protein of paragraph 51, wherein the protein comprises a light chain domain having an amino acid sequence of SEQ ID NO:13, SEQ ID NO:41, SEQ ID NO:42 or SEQ ID NO:43.

58. The VEGF-A-binding protein of paragraph 51, wherein the protein comprises a heavy chain domain having an amino acid sequence of SEQ ID NO:14 or SEQ ID NO:44.

59. The VEGF-A-binding protein of paragraph 51, wherein the protein comprises an Fc domain having an amino acid sequence of SEQ ID NO:27, SEQ ID NO:28, SEQ ID NO:29, or SEQ ID NO:30.

60. A VEGF-A-binding protein comprising:
a light chain domain having an amino acid sequence of SEQ ID NO:8 modified to include at least one amino acid substitution selected from $F_{50}D$, $V_{110}K$, $L_{154}K$, $L_{154}D$ and $L_{201}K$; and/or
a heavy chain domain having an amino acid sequence of SEQ ID NO:9 modified to include at least one amino acid substitution selected from $V_5K$, $L_{180}S$ and $L_{91}K$; and/or an Fc domain having an amino acid sequence of SEQ ID NO:10 modified to include at least one amino acid substitution selected from $L_{17}K$, $I_{35}K$, $V_{64}K$ and $L_{91}K$.

61. The VEGF-A-binding protein of paragraph 60, wherein the protein comprises a light chain domain having an amino acid sequence of SEQ ID NO:8 modified to include at least two amino acid substitutions; and/or a heavy chain domain having an amino acid sequence of SEQ ID NO:9 modified to include at least two amino acid substitutions; and/or an Fc domain having an amino acid sequence of SEQ ID NO:10 modified to include at least two amino acid substitutions.

62. The VEGF-A-binding protein of paragraph 60 or 61, wherein the protein comprises a light chain domain having an amino acid sequence of SEQ ID NO:8, a heavy chain domain having an amino acid sequence of SEQ ID NO:9, a human IgG Fc domain, or an Fc domain having an amino acid sequence of SEQ ID NO:10.

63. The VEGF-A-binding protein of paragraph 60, wherein the protein comprises a light chain domain having an amino acid sequence of SEQ ID NO:11, SEQ ID NO:45, SEQ ID NO:46, SEQ ID NO:47 or SEQ ID NO:48.

64. The VEGF-A-binding protein of paragraph 60, wherein the protein comprises a heavy chain domain having an amino acid sequence of SEQ ID NO:12, SEQ ID NO:49 or SEQ ID NO:50.

65. The VEGF-A-binding protein of paragraph 60, comprising an Fc domain having an amino acid sequence of SEQ ID NO:23, SEQ ID NO:24, SEQ ID NO:25, or SEQ ID NO:26.

66. The VEGF-A-binding protein of any of paragraphs 51-65, wherein the protein is in the form of a monoclonal antibody 67. The VEGF-A-binding protein of paragraph 66, wherein the monoclonal antibody is a chimeric, human or humanized monoclonal antibody.

68. The VEGF-A-binding protein of any of paragraphs 51-65, wherein the protein is in the form of a fusion protein.

69. The VEGF-A-binding protein of any of paragraphs 51-65, wherein the protein is in the form of an Fab antibody fragment, single-chain Fv antibody fragment, or minibody.

70. The VEGF-A-binding protein of any of paragraphs 51-69, wherein the protein is conjugated to a diagnostic agent or a therapeutic agent.

71. A composition comprising the VEGF-A-binding protein of any of paragraphs 51-70.

72. The composition of paragraph 71, wherein the protein is present at a concentration of about 50 mg/ml to about 250 mg/ml.

73. The composition of paragraph 72, wherein the protein is present at a concentration of about 100 mg/ml to about 200 mg/ml.

74. The composition of paragraph 73, wherein the protein is present at a concentration of about 110 mg/ml to about 150 mg/ml.

75. The composition of paragraph 74, wherein the protein is present at a concentration of about 120 mg/ml.

76. The composition of paragraph 74, wherein the protein is present at a concentration of about 130 mg/ml.

77. The composition of any of paragraphs 71-76, wherein the composition further comprises at least one buffer, at least one stabilizer, and/or at least one surfactant.

78. The composition of any of paragraphs 71-77, wherein the composition is liquid.

79. The composition of paragraph 78, wherein the composition is formulated for subcutaneous injection.

80. The composition of any of paragraphs 71-79, wherein the composition is sterile.

81. The composition of any of paragraphs 71-80, wherein the composition further comprises histidine HCl, trehalose dehydrate, methionine and/or polysorbate.

82. The composition of paragraph 71, wherein the composition comprises about 110 to about 130 mg/ml VEGF-A-binding protein, about 10 mM to about 30 mM histidine HCl, about 200 mM to about 220 mM trehalose dehydrate, about 5 mM to about 15 mM methionine, and/or about 0.04% to about 0.08% polysorbate 80.

83. A method of treating a condition in a subject in need thereof, comprising administering to the subject a therapeutically effective amount of the composition of any of paragraphs 71-82.

84. The method of paragraph 83, wherein the condition is cancer.

85. The method of paragraph 84, wherein the cancer is colorectal cancer, lung cancer, breast cancer, glioblastoma, kidney cancer, or ovarian cancer.

86. A nucleic acid encoding the VEGF-A-binding protein of any of paragraphs 51-70.

87. A vector comprising the nucleic acid of paragraph 86.

88. An expression cassette comprising the nucleic acid of paragraph 86.

89. A host cell comprising the nucleic acid of paragraph 86, the vector of paragraph 87, or the expression cassette of paragraph 88.

90. A method of producing an antibody, comprising culturing the host cell of paragraph 89.

91. A kit comprising a container and the VEGF-A-binding protein of any of paragraphs 51-70 or the composition of any of paragraphs 71-82 contained therein.

92. The kit of paragraph 91, wherein the container is glass or plastic. 93. The kit of paragraph 91 or 92, wherein the container is a vial or a syringe. 94. The kit of any of paragraphs 91-93, wherein the kit further comprises instructions for using the kit.

95. The kit of any of paragraphs 91-94, wherein the kit further comprises a package insert or label indicating that the protein or composition can be used to treat cancer characterized by the overexpression of VEGF-A.

96. The kit of any of paragraphs 91-95, wherein the composition is provided at a volume of less than about 2 ml or is about 2 ml.

97. The kit of paragraph 96, wherein the composition is provided at a volume of about 1.5 ml.

Example

Changes in aggregation tendency were assessed for several VEGF-A-binding proteins, each having an amino acid substitution. The proteins were formulated in 10 mM histidine HCl (pH 6.5) and concentrated to 50 mg/ml. To evaluate aggregation, solutions of each protein were incubated at an elevated temperature and analyzed (FIG. 1).

| SEQUENCES |
| --- |

SEQ ID NO: 1
DIQMTQSPSS LSASVGDRVT ITC<u>RASQDVN TAVAW</u>YQQKP GKAPKLLIYS <u>ASFLYS</u>GVPS RFSGSRSGTD
FTLTISSLQP EDFATYYC<u>QQ HYTTPPTFGQ</u> GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGEC

SEQ ID NO: 2
EVQLVESGGG LVQPGGSLRL SCAAS<u>GFNIK DTYIH</u>WVRQA PGKGLEWVAR <u>IYPTNGYTRY ADSVKG</u>RFTI
SADTSKNTAY LQMNSLRAED TAVYYCSR<u>WG GDGFYAMDY</u>W GQGTLVTVSS ASTKGPSVFP LAPSSKSTSG
GTAALGCLVK DYFPEPVTVS WNSGALTSGV HTFPAVLQSS GLYSLSSVVT VPSSSLGTQT YICNVNHKPS
NTKVDKKVEP

SEQ ID NO: 3
PKSCDKTHTC PPCPAPELLG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVFWESNGQ PENNYKTTPP VLDSDGSFFL YSKLTVDKSR WQQGNVFSCS
VMHEALHNHY TQKSLSLSPG K

SEQ ID NO: 4
DIQMTQSPSS LSASVGDRVT ITCRASQDVN TAVAWYQQKP GKAPKLLIYS ASFLYSGVPS RFSGSRSGTD
FTLTISSLQP EDFATYYCQQ HYTTPPTFGQ GTKVEIKRTV AAPSVFIFPP SDEQLKSGTA SVVCLLNNFY
PREAKVQWKV DNASQSGNSQ ESVTEQDSKD STYSLSSTLT LSKADYEKHK VYACEVTHQG LSSPVTKSFN
RGEC

SEQ ID NO: 5
EVQLVESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDYW GQGTLVTVSS ASTKGPSVFP LAPSSKSTSG
GTAALGCLVK DYFPEPVTVS WNSGALTSGV HTFPAVSQSS GLYSLSSVVT VPSSSLGTQT YICNVNHKPS
NTKVDKKVEP

SEQ ID NO: 6
DIQMTQSPSS LSASVGDRVT ITCRASQDVN TAVAWYQQKP GKAPKLLIYS ASFLYSGVPS RFSGSRSGTD
FTLTISSLQP EDFATYYCQQ HYTTPPTFGQ GTKVEIKRTV AAPSVFIFPP SDEQLKSGTA SVVCLLNNFY
PREAKVQWKV DNAXQSGNSQ ESVTEQDSKD STYSLSSTLT LSKADYEKHK VYACEVTHQG LSSPVTKSFN
RGEC

SEQ ID NO: 7
EVQLVESGGG LVQPGGSLRL SCAASGFNIK DTYIHWVRQA PGKGLEWVAR IYPTNGYTRY ADSVKGRFTI
SADISKNIAY LQMNSLRAED TAVYYCSRWG GDGFYAMDYW GQGTLVIVSS ASTKGPSVFP LAPSSKSTSG
GTAALGCLVK DYFPEPVTVS WNSGALTSGV HTFPAVXQSS GLYSLSSVVT VPSSSLGTQT YICNVNHKPS
NTKVDKKVEP

SEQ ID NO: 8
DIQMTQSPSS LSASVGDRVT ITC<u>SASQDIS NYLN</u>WYQQKP GKAPKVLIYF <u>TSSLHS</u>GVPS RFSGSGSGTD
FTLTISSLQP EDFATYYC<u>QQ YSTVPWT</u>FGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGE

SEQ ID NO: 9
EVQLVESGGG LVQPGGSLRL SCAAS<u>GYTFT NYGMN</u>WVRQA PGKGLEWVGW <u>INTYTGEPTY AADFKRR</u>FTF
SLDTSKSTAY LQMNSLRAED TAVYYCAK<u>YP HYYGSSHWYF DV</u>WGQGTLVT VSSASTKGPS VFPLAPSSKS
TSGGTAALGC LVKDYFPEPV TVSWNSGALT SGVHTFPAVL QSSGLYSLSS VVTVPSSSLG TQTYICNVNH
KPSNTKVDKK VEPK

SEQ ID NO: 10
SCDKTHTCPP CPAPELLGGP SVFLFPPKPK DTLMISRTPE VTCVVVDVSH EDPEVKFNWY VDGVEVHNAK
TKPREEYNS TYRVVSVLTV LHQDWLNGKE YKCKVSNKAL PAPIEKTISK AKGQPREPQV YILPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 11
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNADQSGNSQ ESVTEQDSKD STYSLSSTLT LSKADYEKHK VYACEVTHQG LSSPVTKSFN
RGE

SEQ ID NO: 12
EVQLVESGGG LVQPGGSLRL SCAASGYTFT NYGMNWVRQA PGKGLEWVGW INTYTGEPTY AADFKRRFTF
SLDTSKSTAY LQMNSLRAED TAVYYCAKYP HYYGSSHWYF DVWGQGTLVT VSSASTKGPS VFPLAPSSKS
TSGGTAALGC LVKDYFPEPV TVSWNSGALT SGVHTFPAVS QSSGLYSLSS VVTVPSSSLG TQTYICNVNH
KPSNTKVDKK VEPK

SEQ ID NO: 13
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNAXQSGNSQ ESVTEQDSKD STYSLSSTLT LSKADYEKHK VYACEVTHQG LSSPVTKSFN
RGE

SEQ ID NO: 14
EVQLVESGGG LVQPGGSLRL SCAASGYTFT NYGMNWVRQA PGKGLEWVGW INTYTGEPTY AADFKRRFTF
SLDTSKSTAY LQMNSLRAED TAVYYCAKYP HYYGSSHWYF DVWGQGTLVT VSSASTKGPS VFPLAPSSKS
TSGGTAALGC LVKDYFPEPV TVSWNSGALT SGVHTFPAVX QSSGLYSLSS VVTVPSSSLG TQTYICNVNH
KPSNTKVDKK VEPK

SEQ ID NO: 15
PKSCDKTHTC PPCPAPELKG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL YSKLTVDKSR WQQGNVFSCS
VMHEALHNHY TQKSLSLSPG K

SEQ ID NO: 16
PKSCDKTHTC PPCPAPELLG GPSVFLFPPK PKDTLMKSRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL YSKLTVDKSR WQQGNVFSCS
VMHEALHNHY TQKSLSLSPG K

SEQ ID NO: 17
PKSCDKTHTC PPCPAPELLG GPSVFLFPPK PKDTLMISRT PEVTCVVVDV SHEDPEKKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL YSKLTVDKSR WQQGNVFSCS
VMHEALHNHY TQKSLSLSPG K

SEQ ID NO: 18
PKSCDKTHTC PPCPAPELLG GPSVFLFPPK PKDTLMISRT PEVTCVVVDV SHEDPEVKFN WYVDGVEVHN
AKTKPREEQY NSTYRVVSVL TVKHQDWLNG KEYKCKVSNK ALPAPIEKTI SKAKGQPREP QVYTLPPSRD
ELTKNQVSLT CLVKGFYPSD IAVEWESNGQ PENNYKTTPP VLDSDGSFFL YSKLTVDKSR WQQGNVFSCS
VMHEALHNHY TQKSLSLSPG K

SEQ ID NO: 19
PKSCDKTHTC PPCPAPELXG GPSVFLFPPK PKDTLMISRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTIPP VLDSDGSFFL YSKLTVDKSR WQQGNVFSCS
VMHEALHNHY TQKSLSLSPG K

SEQ ID NO: 20
PKSCDKTHTC PPCPAPELLG GPSVFLFPPK PKDTLMXSRT PEVTCVVVDV SHEDPEVKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTIPP VLDSDGSFFL YSKLTVDKSR WQQGNVFSCS
VMHEALHNHY TQKSLSLSPG K

SEQ ID NO: 21
PKSCDKTHTC PPCPAPELLG GPSVFLFPPK PKDTLMISRT PEVTCVVVDV SHEDPEXKFN WYVDGVEVHN
AKTKPREEQY NSTYRVVSVL TVLHQDWLNG KEYKCKVSNK ALPAPIEKTI SKAKGQPREP QVYTLPPSRD
ELTKNQVSLT CLVKGFYPSD IAVEWESNGQ PENNYKTIPP VLDSDGSFFL YSKLTVDKSR WQQGNVFSCS
VMHEALHNHY TQKSLSLSPG K

SEQ ID NO: 22
PKSCDKTHTC PPCPAPELLG GPSVFLFPPK PKDTLMISRT PEVTCVVVDV SHEDPEVKFN WYVDGVEVHN
AKTKPREEQY NSTYRVVSVL TVXHQDWLNG KEYKCKVSNK ALPAPIEKTI SKAKGQPREP QVYTLPPSRD
ELTKNQVSLT CLVKGFYPSD IAVEWESNGQ PENNYKTIPP VLDSDGSFFL YSKLTVDKSR WQQGNVFSCS
VMHEALHNHY TQKSLSLSPG K

SEQ ID NO: 23
SCDKTHTCPP CPAPELKGGP SVFLFPPKPK DTLMISRTPE VTCVVVDVSH EDPEVKFNWY VDGVEVHNAK
TKPREEQYNS TYRVVSVLTV LHQDWLNGKE YKCKVSNKAL PAPIEKTISK AKGQPREPQV YILPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 24
SCDKTHTCPP CPAPELLGGP SVFLFPPKPK DTLMKSRTPE VTCVVVDVSH EDPEVKFNWY VDGVEVHNAK
TKPREEQYNS TYRVVSVLTV LHQDWLNGKE YKCKVSNKAL PAPIEKTISK AKGQPREPQV YILPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 25
SCDKTHTCPP CPAPELLGGP SVFLFPPKPK DTLMISRTPE VTCVVVDVSH EDPEVKFNWY VDGKEVHNAK
TKPREEQYNS TYRVVSVLTV LHQDWLNGKE YKCKVSNKAL PAPIEKTISK AKGQPREPQV YILPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 26
SCDKTHTCPP CPAPELLGGP SVFLFPPKPK DTLMISRTPE VTCVVVDVSH EDPEVKFNWY VDGVEVHNAK
TKPREEQYNS TYRVVSVLTV KHQDWLNGKE YKCKVSNKAL PAPIEKTISK AKGQPREPQV YILPPSRDEL

```
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 27
SCDKTHTCPP CPAPELXGGP SVFLFPPKPK DTLMISRTPE VTCVVVDVSH EDPEVKFNWY VDGVEVHNAK
TKPREEQYNS TYRVVSVLTV LHQDWLNGKE YKCKVSNKAL PAPIEKTISK AKGQPREPQV YILPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 28
SCDKTHTCPP CPAPELLGGP SVFLFPPKPK DTLMXSRTPE VTCVVVDVSH EDPEVKFNWY VDGVEVHNAK
TKPREEQYNS TYRVVSVLTV LHQDWLNGKE YKCKVSNKAL PAPIEKTISK AKGQPREPQV YTLPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 29
SCDKTHTCPP CPAPELLGGP SVFLFPPKPK DTLMISRTPE VTCVVVDVSH EDPEVKFNWY VDGXEVHNAK
TKPREEQYNS TYRVVSVLTV LHQDWLNGKE YKCKVSNKAL PAPIEKTISK AKGQPREPQV YTLPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 30
SCDKTHTCPP CPAPELLGGP SVFLFPPKPK DTLMISRTPE VTCVVVDVSH EDPEVKFNWY VDGVEVHNAK
TKPREEQYNS TYRVVSVLTV XHQDWLNGKE YKCKVSNKAL PAPIEKTISK AKGQPREPQV YTLPPSRDEL
TKNQVSLTCL VKGFYPSDIA VEWESNGQPE NNYKTTPPVL DSDGSFFLYS KLTVDKSRWQ QGNVFSCSVM
HEALHNHYTQ KSLSLSPGK

SEQ ID NO: 31
MELAALCRWGLLLALLPPGAASTQVCTGTDMKLRLPASPETHLDMLRHLYQGCQVVQGNLELTYLPTNASLSFLQD
IQEVQGYVLIAHNQVRQVPLQRLRIVRGTQLFEDNYALAVLDNGDPLNNTTPVTGASPGGLRELQLRSLTEILKGG
VLIQRNPQLCYQDTILWKDIFHKNNQLALTLIDTNRSRACHPCSPMCKGSRCWGESSEDCQSLTRTVCAGGCARCK
GPLPTDCCHEQCAAGCTGPKHSDCLACLHFNHSGICELHCPALVTYNTDTFESMPNPEGRYTFGASCVTACPYNYL
STDVGSCTLVCPLHNQEVTAEDGTQRCEKCSKPCARVCYGLGMEHLREVRAVTSANIQEFAGCKKIFGSLAFLPES
FDGDPASNTAPLQPEQLQVFETLEEITGYLYISAWPDSLPDLSVFQNLQVIRGRILHNGAYSLTLQGLGISWLGLR
SLRELGSGLALIHHNTHLCFVHTVPWDQLFRNPHQALLHTANRPEDECVGEGLACHQLCARGHCWGPGPTQCVNCS
QFLRGQECVEECRVLQGLPREYVNARHCLPCHPECQPQNGSVTCFGPEADQCVACAHYKDPPFCVARCPSGVKPDL
SYMPIWKFPDEEGACQPCPINCTHSCVDLDDKGCPAEQRASPLTSIISAVVGILLVVLGVVFGILIKRRQQKIRK
YTMRRLLQETELVEPLTPSGAMPNQAQMRILKETELRKVKVLGSGAFGTVYKGIWIPDGENVKIPVAIKVLRENTS
PKANKEILDEAYVMAGVGSPYVSRLLGICLTSTVQLVTQLMPYGCLLDHVRENRGRLGSQDLLNWCMQIAKGMSYL
EDVRLVHRDLAARNVLVKSPNHVKITDFGLARLLDIDETEYHADGGKVPIKWMALESILRRRFTHQSDVWSYGVTV
WELMTFGAKPYDGIPAREIPDLLEKGERLPQPPICTIDVYMIMVKCWMIDSECRPRFRELVSEFSRMARDPQRFVV
IQNEDLGPASPLDSTFYRSLLEDDDMGDLVDAEEYLVPQQGFFCPDDPAPGAGGMVHHRHRSSSTRSGGGDLTLGLE
PSEEEAPRSPLAPSEGAGSDVFDGDLGMGAAKGLQSLPTHDPSPLQRYSEDPTVPLPSETDGYVAPLTCSPQPEYV
NQPDVRPQPPSPREGPLPAARPAGATLERPKTLSPGKNGVVKDVFAFGGAVENPEYLTPQGGAAPQPHPPPAFSPA
FDNLYYWDQDPPERGAPPSIFKGIPTAENPEYLGLDVPV

SEQ ID NO: 32
MNFLLSWVHWSLALLLYLHHAKWSQAAPMAEGGGQNHHEVVKFMDVYQRSYCHPIETLVDIFQEYPDEIEYIFKPS
CVPLMRCGGCCNDEGLECVPTEESNITMQIMRIKPHQGQHIGEMSFLQHNKCECRPKKDRARQEKKSVRGKGKGQK
RKRKKSRYKSWSVYVGARCCLMPWSLPGPHPCGPCSERRKHLFVQDPQTCKCSCKNTDSRCKARQLELNERTCRCD
KPRR

SEQ ID NO: 33
GTCGACATGGGTTGGAGCCTCATCTTGCTCTTCCTTGTCGCTGTTGCTACGCGTGTCCTGTCCGACATCCAGATGA
CTCAGAGCCCAAGCAGCTTGTCTGCAAGCGTGGGCGACCGAGTGACAATCACCTGTAGGGCCTCACAGGACGTGAA
CACCGCTGTGGCCTGGTATCAACAGAAGCCCGGCAAGGCCCCCAAACTGCTTATCTATAGCGCCAGCTTCCTGTAT
AGCGGCGTGCCCTCTAGGTTCAGCGGCTCAAGGAGCGGCACGGATTTTACCTTGACCATCTCTTCCCTGCAGCCCG
AAGACTTCGCCACTTACTACTGCCAGCAGCACTACACCACTCCCCCTACCTTCGGCCAAGGCACGAAAGTGGAGAT
CAAGAGGACTGTTGCAGCGCCCAGCGTTTTCATCTTTCCGCCCAGTGACGAGCAGCTGAAGTCTGGCACGGCCTCC
GTGGTGTGCCTGCTGAACAACTTCTACCCGAGGGAGGCGAAGGTCCAATGGAAGGTGGACAACGCCCTGCAATCCG
GCAACAGCCAAGAGAGCGTGACGGAGCAGGATAGCAAGGACAGCACGTACAGCCTGTCTAGCACCCTGACGTTGAG
CAAGGCGGACTACGAAAAGCACAAGGTGTACGCCTGCGAGGTCACGCATCAAGGTCTGAGCAGCCCCGTGACCAAG
AGCTTCAACAGGGGCGAGTGCTAAGCGGCCGC

SEQ ID NO: 34
GTCGACATGGGTTGGAGCCTCATCTTGCTCTTCCTTGTCGCTGTTGCTACGCGTGTCCTGTCCGAAGTGCAGTTGG
TGGAGAGCGGAGGCGGCCTGGTCCAGCCGGGAGGCAGCCTGCGATTGTCATGTGCTGCGAGCGGTTTCAACATCAA
GGACACGTATATCCATTGGGTCAGGCAAGCTCCTGGGAAAGGCCTCGAGTGGGTCGCCAGGATCTACCCGACCAAC
GGCTACACCAGGTACGCCGACAGTGTGAAAGGCAGGTTCACCATCAGCGCCGATACCAGCAAGAACACGGCCTACC
TTCAGATGAACTCCCTTCGCGCGGAAGATACGGCGGTTTATTACTGTTCAAGATGGGGCGGAGACGGCTTCTACGC
CATGGACTACTGGGGCCAGGGCACTCTGGTCACAGTGTCCAGCGCGAGCACCAAAGGCCCGAGCGTCTTCCCTCTT
GCCCCCAGCAGCAAATCAACCAGCGGTGGGACAGCGTCCCTGGGGTGCCTGGTAAAGATTACTTTCCGGAGCCCG
TGACGGTGTCCTGAACAGTGGGGCCCTGACGAGCGGCGTGCATACCTTCCCAGCCGTGCTTCAAAGCAGCGGGCT
CTACTCCCTGAGCTCCGTAGTGACCGTCCCTAGTAGTAGCCTGGCACCCAAACCTACATCTGCAACGTCAACCAT
AAGCCCAGCAACACCAAGGTTGACAAGAAGGTGGAGCCCCCAAGTCATGCGACAAGACGCACACCTGTCCCCCAT
GCCCGGCACCCGAGCTTTTGGGAGGGCCCAGCGTGTTCCTGTTCCCCCCGAAGCCCAAGGATACTCTGATGATCAG
CCGCACCCCGGAGGTAACTTGCGTGGTGGTGGATGTAAGCCACGAGGACCCGGAAGTGAAGTTCAACTGGTACGTG
```

| SEQUENCES |
| --- |
| GACGGCGTGGAGGTGCACAACGCCAAAACTAAGCCGAGAGAGGAGCAGTATAACAGCACCTACAGGGTGGTGTCAG
TCCTCACGGTGCTGCACCAAGACTGGCTGAACGGCAAAGAGTACAAGTGCAAGGTGAGCAACAAAGCCCTGCCAGC
GCCCATCGAGAAGACAATCAGCAAGGCCAAAGGACAGCCCAGGGAACCGCAGGTTTATACCCTGCCCCCCTCCCGC
GACGAGCTTACCAAGAACCAGGTCAGCCTGACTTGCCTCGTCAAGGGGTTTTATCCCAGTGACATCGCCGTCGAAT
GGGAGAGCAACGGCCAACCCGAGAACAACTACAAGACCACGCCCCCTGTGCTTGACAGCGACGGATCATTCTTTCT
GTACAGCAAGCTGACCGTGGACAAAAGCCGGTGGCAACAGGGCAATGTGTTTAGCTGTTCTGTGATGCATGAGGCG
CTTCACAACCATTACACCCAGAAGAGCCTGTCTCTGAGTCCCGGTAAATAAGC*GGCCGC*

SEQ ID NO: 35
*GTCGAC*ATGGGTTGGAGCCTCATCTTGCTCTTCCTTGTCGCTGTTGCTACGCGTGTCCTGTCCGACATCCAGATGA
CCCAAAGCCCCAGCTCTCTGAGCGCGAGCGTGGGCGACAGGGTGACGATCACCTGCAGCGCAAGCCAGGACATCAG
CAACTACCTCAACTGGTATCAGCAGAAGCCCGGCAAGGCTCCCAAGGTCCTGATCTACTTCACCAGCAGCCTCCAC
AGCGGCGTACCCAGCAGGTTCAGCGGCAGCGGCTCTGGGACCGATTTCACCCTCACCATCAGCTCCCTGCAACCCG
AAGACTTCGCCACCTACTACTGCCAACAGTACTCCACCGTGCCCTGGACCTTTGGGCAGGGAACCAAAGTCGAGAT
CAAGAGGACCGTGGCTGCGCCCAGCGTGTTCATTTTCCCCCCGAGCGACGAGCAGCTGAAGTCCGGCACCGCCAGC
GTCGTGTGCCTGCTGAACAACTTCTACCCCAGGGAAGCCAAGGTGCAGTGGAAGGTGGACAACGCCCTGCAGAGCG
GCAACTCCCAGGAGAGCGTAACCGAGCAGGACAGCAAGGACAGTACCTACAGCCTGAGCAGCACACTGACCCTTAG
CAAGGCCGACTACGAGAAGCACAAGGTGTACGCCTGCGAGGTGACCCATCAGGGTCTGAGCTCTCCCGTGACCAAG
AGCTTCAACAGGGGCGAGTGCTGAGC*GGCCGC*

SEQ ID NO: 36
*GTCGAC*ATGGGTTGGAGCCTCATCTTGCTCTTCCTTGTCGCTGTTGCTACGCGTGTCCTGTCCGAGGTGCAACTCG
TAGAGAGTGGCGGTGGGCTGGTCCAGCCAGGCGGCTCATTGAGGCTTTCATGTGCTGCCAGCGGTTACACGTTCAC
CAACTATATGGCATGAACTGGGTCAGGCAGGCTCCCGGAAAGGGCTTGGAGTGGGTGGGGTGGATCAATACGTACACC
GGCGAACCGACCTACGCTGCCGACTTTAAGAGAAGGTTCACCTTCAGCCTGGACACCAGCAAGTCAACCGCTTACC
TGCAAATGAACAGTCTGAGGGCCGAGGACACGGCCGGTCTACTACTGCGCCAAGTACCCCATTACTACGGGAGCAG
CCATTGGTACTTCGACGTTTGGGGCCAGGGCACGCTGGTCACAGTGAGCTCCGCCTCAACGAAAGGTCCGTCCGTC
TTCCCCCTGGCTCCTAGCTCTAAGAGCACGTCCGGGGGAACGGCTGCGCTGGGGTGCCTGGTAAAGGATTACTTCC
CGGAGCCCGTCACCGTGAGCTGGAACAGCGGTGCGCTGACGAGCGGCGTGCACACATTTCCTGCCGTCCTGCAGTC
CTCCGGGCTTTACTCCCTCAGCAGCGTCGTGACGGTCCCAAGCAGCAGCCTTGGCACACAGACCTACATCTGCAAC
GTGAACCACAAGCCCTCCAACACGAAGGTGGACAAGAAAGTTGAGCCCAAGAGCTGCGATAAAACTCACACCTGTC
CCCCGTGCCCCGCACCCGAGCTCCTGGGCGGACCGAGCGTGTTCCTGTTCCCGCCTAAGCCGAAAGATACCCTGAT
GATCAGCCGAACCCCCGAGGTCACATGCGTGGTGGTGGACGTGAGCCACGAGGATCCCGAAGTGAAGTTCAACTGG
TACGTGGACGGCGTGGAGGTCCACAACGCCAAGACGAAACCCCGGGAGGAGCAGTACAACAGCACCTACAGGGTGG
TGAGCGTGCTGACAGTGCTGCATCAGGACTGGTTGAACGGCAAGGAGTACAAGTGCAAGGTCAGCAACAAAGCACT
GCCTGCGCCGATCGAGAAGACCATCAGCAAGGCCAAGGGCCAACCCAGGGAGCCCCAGGTGTATACCCTTCCGCCA
AGCCGGGACGAATTGACGAAGAACCAGGTCTCACTTACTTGCCTCGTCAAGGGCTTCTACCCCTCCGACATCGCCG
TGGAATGGGAGAGCAACGGGCAACCCGAGAACAACTACAAGACCACCCCGCCAGTTTTGGACAGCGACGGCTCTTT
CTTCCTCTACAGCAAGCTGACCGTTGACAAGAGCAGGTGGCAACAGGGAAACGTGTTCAGCTGCAGTGTGATGCAC
GAGGCCCTGCACAACCACTACACCCAGAAATCACTGTCTCTGTCACCCGGCAAGTGA*GCGGCCGC*

SEQ ID NO: 37
EVQLXESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDYW GQGTLVTVSS ASTKGPSVFP LAPSSKSTSG
GTAALGCLVK DYFPEPVTVS WNSGALTSGV HTFPAVLQSS GLYSLSSVVT VPSSSLGTQT YICNVNHKPS
NTKVDKKVEP

SEQ ID NO: 38
DIQMTQSPSS LSASVGDRVT ITCRASQDVN TAVAWYQQKP GKAPKLLIYS ASFLYSGVPS RFSGSRSGTD
FTLTISSLQP EDFATYYCQQ HYTTPPTFGQ GTKVEIKRTV AAPSVFIFPP SDEQLKSGTA SVVCLLNNFY
PREAKVQWKV DNAKQSGNSQ ESVTEQDSKD STYSLSSTLT LSKADYEKHK VYACEVTHQG LSSPVTKSFN
RGEC

SEQ ID NO: 39
EVQLKESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDYW GQGTLVTVSS ASTKGPSVFP LAPSSKSTSG
GTAALGCLVK DYFPEPVTVS WNSGALTSGV HTFPAVLQSS GLYSLSSVVT VPSSSLGTQT YICNVNHKPS
NTKVDKKVEP

SEQ ID NO: 40
EVQLVESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDYW GQGTLVTVSS ASTKGPSVFP LAPSSKSTSG
GTAALGCLVK DYFPEPVTVS WNSGALTSGV HTFPAVKQSS GLYSLSSVVT VPSSSLGTQT YICNVNHKPS
NTKVDKKVEP

SEQ ID NO: 41
DIQMTQSPSS LSASVGDRVT ITCSASQDIS NYLNWYQQKP GKAPKVLIYX TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGE

SEQ ID NO: 42
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTX AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGE |

-continued

SEQUENCES

SEQ ID NO: 43
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG XSSPVTKSFN
RGE

SEQ ID NO: 44
EVQLXESGGG LVQPGGSLRL SCAASGYTFT NYGMNWVRQA PGKGLEWVGW INTYTGEPTY AADFKRRFTF
SLDTSKSTAY LQMNSLRAED TAVYYCAKYP HYYGSSHWYF DVWGQGTLVT VSSASTKGPS VFPLAPSSKS
TSGGTAALGC LVKDYFPEPV TVSWNSGALT SGVHTFPAVL QSSGLYSLSS VVTVPSSSLG TQTYICNVNH
KPSNTKVDKK VEPK

SEQ ID NO: 45
DIQMTQSPSS LSASVGDRVT ITCSASQDIS NYLNWYQQKP GKAPKVLIYD TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGE

SEQ ID NO: 46
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTK AAPSVFIFPP SDEQLKSGTA SVVCLLNNFY
PREAKVQWKV DNALQSGNSQ ESVTEQDSKD STYSLSSTLT LSKADYEKHK VYACEVTHQG LSSPVTKSFN
RGE

SEQ ID NO: 47
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNAKQSGNSQ ESVTEQDSKD STYSLSSTLT LSKADYEKHK VYACEVTHQG LSSPVTKSFN
RGE

SEQ ID NO: 48
DIQMTQSPSS LSASVGDRVT ITCSASQDIS NYLNWYQQKP GKAPKVLIYF TSSLHSGVPS RFSGSGSGTD
FTLTISSLQP EDFATYYCQQ YSTVPWTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACEVTHQG KSSPVTKSFN
RGE

SEQ ID NO: 49
EVQLKESGGG LVQPGGSLRL SCAASGYTFT NYGMNWVRQA PGKGLEWVGW INTYTGEPTY AADFKRRFTF
SLDTSKSTAY LQMNSLRAED TAVYYCAKYP HYYGSSHWYF DVWGQGTLVT VSSASTKGPS VFPLAPSSKS
TSGGTAALGC LVKDYFPEPV TVSWNSGALT SGVHTFPAVL QSSGLYSLSS VVTVPSSSLG TQTYICNVNH
KPSNTKVDKK VEPK

SEQ ID NO: 50
EVQLVESGGG LVQPGGSLRL SCAASGYTFT NYGMNWVRQA PGKGLEWVGW INTYTGEPTY AADFKRRFTF
SLDTSKSTAY LQMNSLRAED TAVYYCAKYP HYYGSSHWYF DVWGQGTLVT VSSASTKGPS VFPLAPSSKS
TSGGTAALGC LVKDYFPEPV TVSWNSGALT SGVHTFPAVK QSSGLYSLSS VVTVPSSSLG TQTYICNVNH
KPSNTKVDKK VEPK

SEQ ID NO: 51
DIQMTQSPSS LSASVGDRVT ITCRASQDVN TAVAWYQQKP GKAPKLLIYS ASFLYSGVPS RFSGSRSGTD
FTLTISSLQP EDFATYYCQQ HYTTPPTFGQ GTKVEIKRTV AAPSVFIFPP SDEQLKSGTA SVVCLLNNFY
PREAKVQWKV DNALQSGNSQ ESVTEQDSKD STYSLSSTLT LSKADYEKHK VYACNVTHQG LSSPVTKSFN
RGEC

SEQ ID NO: 52
EVQLVESGGG LVQPGGSLRL SCAASGFNIK DTYIHWVRQA PGKGLEWVAR IYPTNGYTRY ADSVKGRFTI
SADTSKNTAY LQMNSLRAED TAVYYCSRWG GDGFYAMDYW GQGTNVTVSS ASTKGPSVFP LAPSSKSTSG
GTAALGCLVK DYFPEPVTVS WNSGALTSGV HTFPAVLQSS GLYSLSSVVT VPSSSLGTQT YICNVNHKPS
NTKVDKKVEP

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A HER2-binding protein comprising:
   a light chain domain, a heavy chain domain and an Fc domain,
   wherein the light chain domain comprises the amino acid sequence of SEQ ID NO:38.

2. The HER2-binding protein of claim 1, wherein the protein comprises a heavy chain domain comprising the amino acid sequence of SEQ ID NO:2.

3. The HER2-binding protein of claim 1, wherein the protein is in the form of a monoclonal antibody or a fusion protein.

4. A composition comprising the HER2-binding protein of claim 1.

5. The composition of claim 4, wherein the protein is present at a concentration of about 50 mg/ml to about 250 mg/ml.

6. A kit comprising a container and the HER2-binding protein of claim 1.

7. The HER2-binding protein of claim 1, wherein the protein comprises a Fc domain comprising the amino acid sequence of SEQ ID NO:3.

8. The HER2-binding protein of claim 1, wherein the heavy chain domain comprises the amino acid sequence of SEQ ID NO:39.

9. The HER2-binding protein of claim 1, wherein the heavy chain domain comprises the amino acid sequence of SEQ ID NO:5.

10. The HER2-binding protein of claim 1, wherein the heavy chain domain comprises the amino acid sequence of SEQ ID NO:40.

11. The HER2-binding protein of claim 1, wherein the heavy chain domain comprises the amino acid sequence of SEQ ID NO:52.

12. The HER2-binding protein of claim 1, wherein the Fc domain comprises the amino acid sequence of SEQ ID NO:15.

13. The HER2-binding protein of claim 1, wherein the Fc domain comprises the amino acid sequence of SEQ ID NO:16.

14. The HER2-binding protein of claim 1, wherein the Fc domain comprises the amino acid sequence of SEQ ID NO:17.

15. The HER2-binding protein of claim 1, wherein the Fc domain comprises the amino acid sequence of SEQ ID NO:18.

* * * * *